US009919034B2

(12) United States Patent
Hodge, III

(10) Patent No.: US 9,919,034 B2
(45) Date of Patent: Mar. 20, 2018

(54) METHODS OF TREATING AND PROPHYLACTICALLY PROTECTING MAMMALIAN PATIENTS INFECTED BY VIRUSES CLASSIFIED IN BALTIMORE GROUP V

(71) Applicant: Tamir Biotechnology, Inc., San Diego, CA (US)

(72) Inventor: Thomas W. Hodge, III, Athens, GA (US)

(73) Assignee: TAMIR BIOTECHNOLOGY, INC., Short Hills, NJ (US)

(*) Notice: Subject to any disclaimer, the term of this patent is extended or adjusted under 35 U.S.C. 154(b) by 0 days.

(21) Appl. No.: 14/736,170

(22) Filed: Jun. 10, 2015

(65) Prior Publication Data

US 2015/0376584 A1     Dec. 31, 2015

Related U.S. Application Data

(63) Continuation-in-part of application No. 14/667,282, filed on Mar. 24, 2015, now abandoned, and a continuation-in-part of application No. 14/316,893, filed on Jun. 27, 2014, now abandoned, which is a continuation-in-part of application No. 14/247,723, filed on Apr. 8, 2014, now abandoned, which is a continuation-in-part of application No. 14/229,816, filed on Mar. 28, 2014, now abandoned.

(60) Provisional application No. 62/147,209, filed on Apr. 14, 2015, provisional application No. 62/102,671, filed on Jan. 13, 2015, provisional application No. 62/063,551, filed on Oct. 14, 2014, provisional application No. 62/040,885, filed on Aug. 22, 2014.

(51) Int. Cl.
| | | |
|---|---|---|
| *C07K 14/005* | (2006.01) | |
| *C07K 7/00* | (2006.01) | |
| *A01N 63/00* | (2006.01) | |
| *C12N 9/22* | (2006.01) | |
| *A61K 38/46* | (2006.01) | |
| *C07H 21/04* | (2006.01) | |

(52) U.S. Cl.
CPC .............. *A61K 38/465* (2013.01); *C12N 9/22* (2013.01); *C12Y 301/27* (2013.01); *C12Y 301/27005* (2013.01); *A01N 63/00* (2013.01)

(58) Field of Classification Search
None
See application file for complete search history.

(56) References Cited

U.S. PATENT DOCUMENTS

| | | |
|---|---|---|
| 4,882,421 A | 11/1989 | Shogen et al. |
| 5,559,212 A | 9/1996 | Ardelt |
| 5,728,805 A | 3/1998 | Ardelt |
| 5,955,073 A | 9/1999 | Rybak et al. |
| 6,175,003 B1 | 1/2001 | Saxena |
| 6,239,257 B1 | 5/2001 | Ardelt |
| 6,423,515 B1 | 7/2002 | Saxena |
| 7,229,824 B2 | 6/2007 | Saxena |
| 7,442,535 B2 | 10/2008 | Saxena |
| 7,442,536 B2 | 10/2008 | Saxena |
| 7,473,542 B2 | 1/2009 | Saxena |
| 7,556,951 B2 | 7/2009 | Saxena |
| 7,556,952 B2 | 7/2009 | Saxena |
| 7,556,953 B2 | 7/2009 | Saxena |
| 7,572,882 B2 | 8/2009 | Sette et al. |
| 7,585,654 B2 | 9/2009 | Saxena |
| 7,585,655 B2 | 9/2009 | Saxena |
| 7,763,449 B2 | 7/2010 | Saxena |
| 8,518,399 B2 | 8/2013 | Saxena |
| 8,663,964 B2 | 3/2014 | Saxena et al. |
| 8,808,690 B2 | 8/2014 | Saxena et al. |
| 9,642,794 B2 | 5/2017 | Sulley et al. |
| 2003/0099629 A1 | 5/2003 | Goldenberg et al. |
| 2004/0072910 A1 | 4/2004 | Porat |
| 2005/0014161 A1 | 1/2005 | Saxena |
| 2007/0231890 A1 | 10/2007 | Saxena |
| 2007/0231891 A1 | 10/2007 | Saxena |
| 2007/0232543 A1 | 10/2007 | Saxena |
| 2007/0232544 A1 | 10/2007 | Saxena |
| 2007/0238861 A1 | 10/2007 | Saxena |
| 2007/0243605 A1 | 10/2007 | Saxena |
| 2007/0243606 A1 | 10/2007 | Saxena |
| 2008/0033151 A1 | 2/2008 | Saxena |
| 2008/0161324 A1 | 7/2008 | Johansen et al. |
| 2009/0081759 A1 | 3/2009 | Saxena |

(Continued)

FOREIGN PATENT DOCUMENTS

| | | |
|---|---|---|
| WO | WO 1996/039428 A1 | 12/1996 |
| WO | WO 1997/031116 A2 | 8/1997 |

(Continued)

OTHER PUBLICATIONS

Tamir Reports Positive Effect Against SARS Virus (Jul. 21, 2010).
Tamir's Compounds Show Remarkable Results Against Dengue Virus (Jul. 19, 2010).
Investor Village—Form 10-Q for Tamir Biotechnology, Inc. (Aug. 15, 2011).
Baltimore, Bacteriological Reviews, vol. 35, No. 3, p. 235-241 (Sep. 1971).
Wikipedia: Baltimore classification (Mar. 6, 2013).
Ilinskaya et al, Molecular Biology, vol. 48, No. 5, pp. 615-623 (2014).
Qiao et al, Cell Research 22:1199-1202 (2012).
Lin et al, Biochemical and Biophysical Research Communications, vol. 204, No. 1, pp. 156-162 (Oct. 14, 1994).
Moreau et al, Antiviral Research 59, pp. 181-191 (2003).
Domachowske et al, Nucleic Acids Research, vol. 26, No. 14, pp. 3358-3363 (1998).

(Continued)

*Primary Examiner* — Nicole Kinsey White
(74) *Attorney, Agent, or Firm* — Mark H. Jay, Esq.

(57) ABSTRACT

Viral infections in mammals can be treated and prophylactically prevented by systemic administration of ranpirnase and three other ribonucleases that are highly homologous with it and that have activities that are highly similar to it. Experimental results against rabies, Middle East Respiratory Syndrome Coronavirus ("MERS-CoV"), influenza, Ebola virus, Chikungunya virus, Venezuelan equine encephalitis, canine parvovirus, adenovirus-2, respiratory syncytial virus, rhinovirus-14, and vaccinia are disclosed.

10 Claims, 32 Drawing Sheets

(56) References Cited

U.S. PATENT DOCUMENTS

| | | |
|---|---|---|
| 2009/0081776 A1 | 3/2009 | Saxena |
| 2009/0081777 A1 | 3/2009 | Saxena |
| 2009/0081778 A1 | 3/2009 | Saxena |
| 2009/0099348 A1 | 4/2009 | Saxena |
| 2009/0111175 A1 | 4/2009 | Saxena |
| 2009/0202513 A1 | 8/2009 | Ramos-Nino et al. |
| 2009/0246214 A1 | 10/2009 | Goldenberg et al. |
| 2010/0291657 A1 | 11/2010 | Saxena |
| 2010/0304463 A1 | 12/2010 | Saxena |
| 2010/0317082 A1 | 12/2010 | Saxena |
| 2011/0274704 A1 | 11/2011 | Chang et al. |
| 2012/0121569 A1 | 5/2012 | Saxena |
| 2012/0149085 A1 | 6/2012 | Goldenberg et al. |
| 2012/0260922 A1 | 10/2012 | Gómez-Acebo et al. |
| 2013/0022589 A1 | 1/2013 | Saxena |
| 2014/0030246 A1 | 1/2014 | Saxena et al. |
| 2014/0037610 A1 | 2/2014 | Saxena et al. |
| 2014/0128396 A1 | 5/2014 | Schadt et al. |
| 2015/0010524 A1 | 1/2015 | Jain |
| 2015/0376584 A1 | 12/2015 | Hodge |
| 2016/0045431 A1 | 2/2016 | Sulley et al. |
| 2016/0045574 A1 | 2/2016 | Sulley et al. |
| 2016/0361392 A1 | 12/2016 | Squiquers et al. |
| 2017/0157219 A1 | 6/2017 | Hodge |
| 2017/0296647 A1 | 10/2017 | Sulley et al. |

FOREIGN PATENT DOCUMENTS

| | | | |
|---|---|---|---|
| WO | WO 1997/038112 A1 | 10/1997 | |
| WO | WO 2000/040608 A1 | 7/2000 | |
| WO | WO 2001/018214 A1 | 3/2001 | |
| WO | WO 2004/061120 A2 | 7/2004 | |
| WO | WO 2005/017100 A2 | 2/2005 | |
| WO | 2005/080586 | 9/2005 | |
| WO | WO 2005/080586 | 9/2005 | |
| WO | WO 2013/039857 A1 | 3/2013 | |
| WO | WO 2013/089835 A1 | 6/2013 | |
| WO | WO 2016/028634 A1 | 8/2015 | |
| WO | WO 2015/148768 A2 | 10/2015 | |
| WO | WO 2016/205109 A1 | 12/2016 | |
| WO | WO 2017/142807 A1 | 8/2017 | |

OTHER PUBLICATIONS

GlobeNewswire, Jul. 21, 2010, Tamir Reports Positive Effect Against SARS Virus.
GlobeNewswire, Jul. 19, 2010, Tamirs Compounds Show Remarkable Results Against Dengue Virus.
InvestorVillage.com, May 15, 2011, ACEL / Message Board/ Thread View.
Baltimore, Expression of Animal Virus Genomes, Bacteriological Reviews, Sep. 1971, vol. 35, No. 3, pp. 235-241.
Wikipedia, Baltimore classification, Mar. 6, 2013.
Ilinskaya, Ribonucleases as Antiviral Agents, Molecular Biology, 2014, vol. 48, No. 5, pp. 615-623.
Qiao, Onconase downregulates microRNA expression through targeting microRNA precursors, Cell Research, 2012, 22:1199-1202.
Lin et al., Biochemical and Biophysical Research Communications 201 (1), 156-162 (1994).
Ardelt et al, Onconase and Amphinase, the Antitumor Ribonucleases from Rana pipiens Oocytes Curr Pharm Biotechnol. Jun. 2008; 9(3): 215-225.
Saxena et al, Effect of Onconase on Double-stranded RNA in Vitr Anticancer Research 29: 1067-1072 (2009).
UniProtKB—Amphinase-2 entry (2007).
PCT/US1999/030799, International Search Report and Written Opinion dated May 30, 2000, 7 pages.
PCT/US2000/023426, International Search Report dated Nov. 27, 2000, 3 pages.
PCT/US2004/014844, International Search Report and Written Opinion, dated May 10, 2006, 8 pages.
PCT/US2004/014844, International Preliminary Report on Patentability, dated Feb. 15, 2007, 5 pages.
PCT/US2015/022670, International Search Report and Written Opinion, dated Nov. 18, 2015, 29 pages.
PCT/US2015/022670, International Preliminary Report on Patentability, dated Oct. 4, 2016, 21 pages.
PCT/US2015/045272, International Search Report and Written Opinion, dated Dec. 1, 2015, 9 pages.
PCT/US2015/045272, International Preliminary Report on Patentability, dated Feb. 21, 2017, 6 pages.
PCT/US2016/037174, International Search Report and Written Opinion, dated Oct. 12, 2016, 14 pages.
Adinolfi, B.S., et al., "Full antitumor action of recombinant seminal ribonuclease depends on the removal of its N-terminal methionine." Biochem Biophys Res Commun. (1995); 213(2): 525-532.
Ardelt, W., et al., "Amino acid sequence of an anti-tumor protein from Rana pipiens oocytes and early embryos. Homology to pancreatic ribonucleases." J Biol Chem. (1991); 266(1): 245-251.
Boix, E., et al., "Role of the N terminus in RNase A homologues: differences in catalytic activity, ribonuclease inhibitor interaction and cytotoxicity." J Mol Biol. (1996); 257(5): 992-1007.
Branden et al., Introduction to Protein Structure, Garland Publishing Inc., New York, p. 247, 1991, 24 pages.
Bucher, M.H., et al., "Differential effects of short affinity tags on the crystallization of Pyrococcus furiosus maltodextrin-binding protein." Acta Crystallogr D Biol Crystallogr. (2002);58(Pt 3): 392-397. Epub Feb. 21, 2002.
Chao, Q., et al., "Expression and partial characterization of Dolichos biflorus seed lectin in *Escherichia coli*." Arch Biochem Biophys. (1994); 313(2): 346-350.
Chaudhuri, T.K., et al., "Effect of the extra n-terminal methionine residue on the stability and folding of recombinant a-lactalbumin expressed in *Escherichia coli*." J Mol Biol. (1999); 285(3): 1179-1194.
Chen, C-Y., et al., "Cloning, sequencing and expression of a cDNA encoding bovine pancreatic deoxyribonuclease I in *Escherichia coli*: purification and characterization of the recombinant enzyme." Gene (1998); 206(2): 181-184.
Durmazlar, K., et al., "Cantharidin treatment for recalcitrant facial flat warts: a preliminary study." J. Dermatol. Treatment (2009); 20(2): 114-119.
Dyer and Rosenberg, "The RNase a superfamily: generation of diversity and innate host defense." Mol Divers. (2006); 10(4): 585-597.
Fonda, I., et al., "Attachment of histidine tags to recombinant tumor necrosis factor-alpha drastically changes its properties." ScientificWorldJournal (2002); 2: 1312-1325.
Geurrero, S.A., et al., "His-tagged tryparedoxin peroxidase of Trypanosoma cruzi as a tool for drug screening." Appl Microbiol Biotechnol. (2000); 53(4): 410-414.
Goda, S., et al., "Effect of extra N-terminal residues on the stability and folding of human lysozyme expressed in Pichia pastoris." Protein Engineering (2000); 13(4): 299-307.
Gupta, P.K., et al., "Role of N-Terminal Amino Acids in the Potency of Anthrax Lethal Factor." PLoS ONE (2008); 3(9): e3130.
Hariri, S., et al., "Human Papillomavirus." Centers for Disease Control VPD Surveillance Manual, 5th edition, Chapter 5, pp. 1 -11 (2011).
Hirel, P.H., et al., "Extent of N-terminal methionine excision from *Escherichia coli* proteins is governed by the side-chain length of the penultimate amino acid." PNAS USA (1989); 86(21): 8247-8251.
Ho, S.N., et al., "Site-directed mutagenesis by overlap extension using the polymerase chain reaction." Gene (1989); 77(1): 51-59.
Huang, H-C., et al., "The Rana catesbeiana rcr Gene Encoding a Cytotoxic Ribonuclease. Tissue Distribution, Cloning, Purification, Cytotoxicity, and Active Residues for RNase Activity." J. Biol. Chem. (1998); 273(11): 6395-6401.
Ishikiwa, N., et al., "Remarkable destabilization of recombinant alpha-lactalbumin by an extraneous N-terminal methionyl residue." Protein Eng. (1998); 11(5): 333-335.
Kamiya, Y., et al., "Amino acid sequence of a lectin from Japanese frog (Rana japonica) eggs." J Biochem. (1990); 108(1): 139-143.
Lehninger, A.L. (1975) Biochemistry, Second Edition, p. 962, 5 pages.

(56) References Cited

OTHER PUBLICATIONS

Liao, Y.D., et al., "Removal of N-terminal methionine from recombinant proteins by engineered E. coli methionine aminopeptidase." Protein Sci. (2004); 13(7): 1802-1810.
Moore, J.A., et al., "Equivalent Potency and Pharmacokinetics of Recombinant Human Growth Hormones with or without an N-Terminal Methionine." Endocrinology (1988); 122(6): 2920-2926.
Mosimann, S.C., et al., "Comparative molecular modeling and crystallization of P-30 protein: A novel antitumor protein of Rana pipiens oocytes and early embryos." Proteins (1992); 14(3): 392-400.
Notomista, E., et al., "Effective expression and purification of recombinant onconase, an antitumor protein." FEBS Letters (1999); 463(3): 211-215.
Park, K.S., et al., "Biologic and biochemic properties of recombinant platelet factor 4 demonstrate identity with the native protein." Blood (1990); 75: 1290-1295.
Porta, C., et al., "Ranpirnase and its potential for the treatment of unresectable malignant mesothelioma." Biologics (2008); 2(4): 601-609.
Saxena, S.K., et al., "Inhibition of HIV-1 production and selective degradation of viral RNA by an amphibian ribonuclease." J Biol Chem. (1996); 271(34): 20783-20788.
Saxena, S.K., et al., "Onconase® and its Therapeutic Potential." Lab Medicine (2003); 34(5): 380-387.
Seffernick, J.L., et al., "Melamine Deaminase and Atrazine Chlorohydrolase: 98 Percent Identical but Functionally Different." Journal of Bacteriology (2001); 183(8): 2405-2410.
Studier, F.W., et al., "Use of T7 RNA polymerase to direct expression of cloned genes." Methods Enzymol. (1990); 185: 60-89.
Suhasini and Sirdeshmukh, "Transfer RNA cleavages by onconase reveal unusual cleavage sites." J Biol Chem. (2006); 281(18): 12201-12209. Epub Feb. 23, 2006.
Supplementary European Search Report in European application No. EP 04751988.9, dated May 30, 2007 and dated Jun. 6, 2007, 6 pages.
Suzuki, M., et al., "Engineering receptor-mediated cytotoxicity into human ribonucleases by steric blockade of inhibitor interaction." Nat Biotechnol. (1999); 17(3): 265-270.
Takano, K., et al., "Effect of foreign N-terminal residues on the conformational stability of human lysozyme." The FEBS Journal (1999); 266(2): 675-682.
Trimble and Frazer, "Development of therapeutic HPV vaccines." Lancet Oncol. (2009); 10(10): 975-980.
Turcotte and Raines, "Design and Characterization of an HIV-Specific Ribonuclease Zymogen." AIDS Res Hum Retroviruses (2008); 24(11): 1357-1363.
Witkowski, A., et al., "Conversion of a β-Ketoacyl Synthase to a Malonyl Decarboxylase by Replacement of the Active-Site Cysteine with Glutamine." Biochemistry, (1999); 38(36): 11643-11650.
Wu and Filutowicz, "Hexahistidine ($His_6$)-tag dependent protein dimerization: a cautionary tale." Acta Biochim Pol. (1999); 46(3): 591-599.
Wu, Y., et al., "A cytotoxic ribonuclease. Study of the mechanism of onconase cytotoxicity." The Journal of Biological Chemistry (1993); 268(14): 10686-10693.
PCT/US2016/037174, International Preliminary Report on Patentability, dated Dec. 19, 2017, 9 pages.
PCT/US2017/043984, International Search Report and Written Opinion, dated Oct. 10, 2017, 15 pages.
Langston, "Herpes Simplex Virus in the Eye", Digital Journal of Ophthalmology, Oct. 15, 2002, 3 pages.

Fig. 1 – Antiviral Activity of Ranpirnase Against Rabies Virus
In Mouse Neuroblastoma Cells ("MNA"), Bat Primary Epithelia Cells ("EF"), and Cloned Baby Hamster Kidney Cells ("BSR")

| | MNA | MNA | MNA | EF | EF | EF | BSR | BSR | BSR |
|---|---|---|---|---|---|---|---|---|---|
| | 24 hours * | 48 hours ** | 72 hours *** | 24 hours * | 48 hours ** | 72 hours *** | 24 hours * | 48 hours ** | 72 hours *** |
| $CC_{50}$ (nM) | | 5005.381 | 2500.2 | | 2250.593 | 65.57339 | | 10378.39 | 1899.458 |
| $IC_{50}$ (nM) | 45.375 | 39.81266 | 18.74693 | 62 | 33.78782 | 25.63462 | 12 | 18.61556 | 18.52307 |
| SI | | 125.7234 | 133.3658 | | 66.60959 | 2.558002 | | 557.5114 | 102.5456 |

* After incubation of ranpirnase, before introduction of rabies virus

** 24 hours after introduction of rabies virus

*** 48 hours after introduction of rabies virus

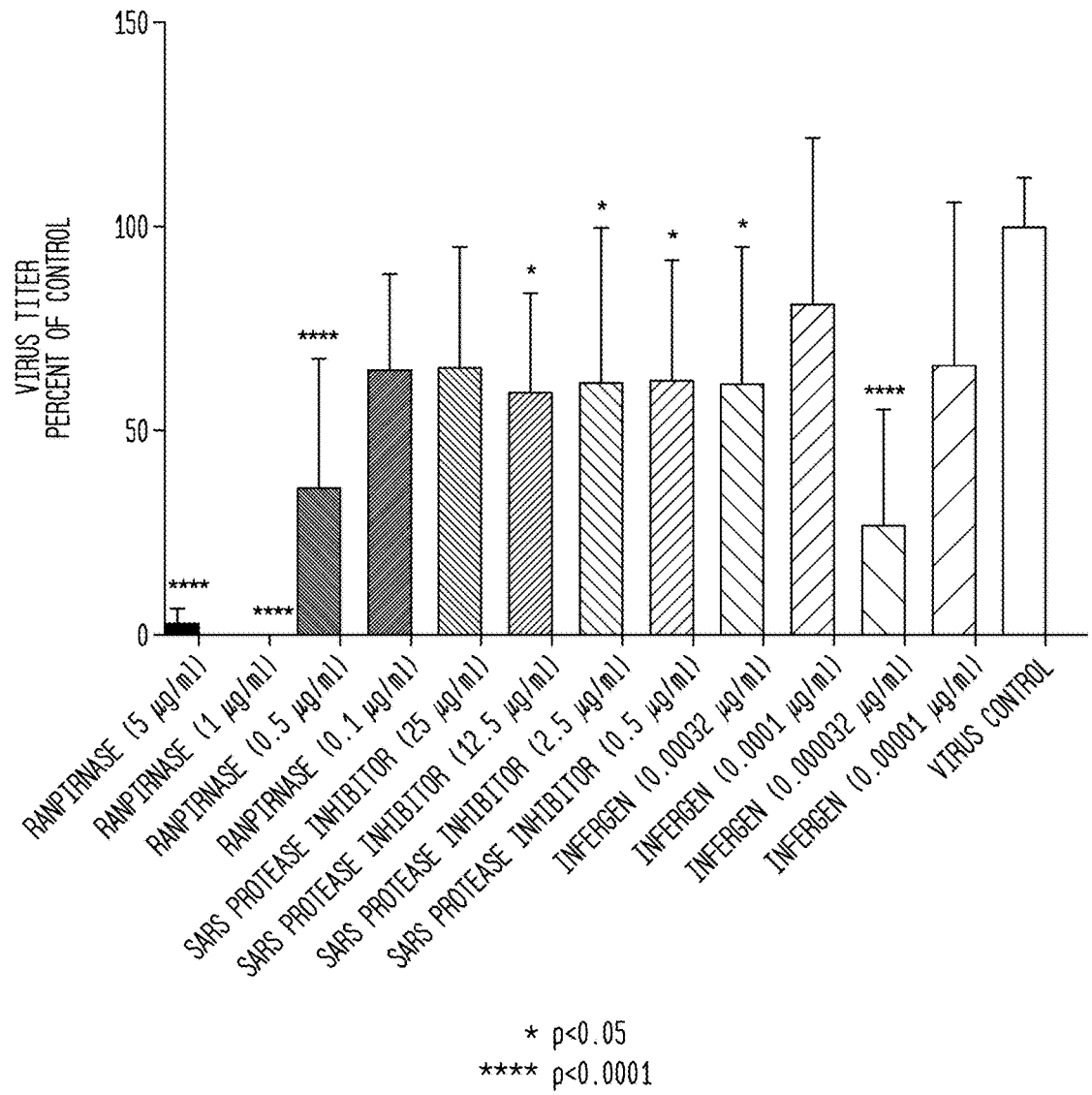

\* p<0.01
\*\* p<0.001
\*\*\* p<0.0001
\*\*\*\* p<0.00001

VEEV+RAN

Figure 4
Results of QC testing in VEEV/Astrocytes

Control inhibitor A

% INH

3000cells/well

| Compound ID | Plate ID | qAC50, M |
|---|---|---|
| Control A, 3k | AA00002015 | 8.60E-07 |
| Control A, 4k | AA00002016 | 7.18E-07 |
| Control A-rep2, 3k | AA00002729 | 8.21E-07 |
| Control A-rep2, 4k | AA00002730 | 1.05E-06 |

Robust statistics for the data on both days of testing

| Index | Plate ID | Cell density / well | Well Masking | Nuclei - Number | % INH | Z' Factor | Number of Analyzed Fields |
|---|---|---|---|---|---|---|---|
| 1 | AA00002729 | 3000 | 0% | 1124.5 | 95.673 | 0.904 | 5 |
| 2 | AA00002730 | 4000 | 0% | 1364.5 | 96.384 | 0.895 | 5 |
| 3 | AA00002015 | 3000 | 0% | 1226.1 | 94.890 | 0.773 | 5 |
| 4 | AA00002016 | 4000 | 0% | 1543.9 | 98.701 | 0.979 | 5 |

Example of image

Infection + Buffer

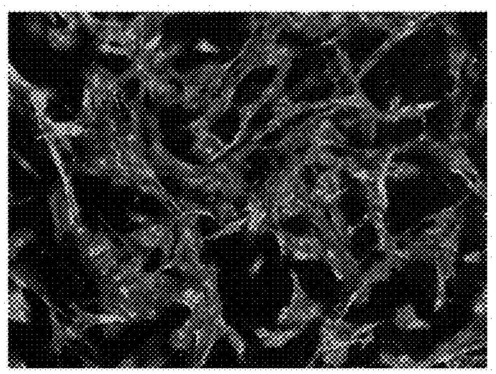

Infection+ 35ug/ml Ranpirnase

Ranpirnase in VEEV/Astrocytes

Figure 6
Results of QC testing in VEEV/HeLa

*VEEV+RAN*

Control Inhibitor E

Figure 7
Ranpirnase in VEEV/HeLa

RAN = Ranpirnase (solution)

RAN-2 = Ranpirnase (powder)

VEEV+RAN

No indication of any type of cytotoxicity in HeLa cells during 20h incubation

Figure 8
Results of QC testing in CHIV/U2OS
*CHIV+RAN*
*Control inhibitor E*
% INH
Robust statistics for the data on both days of testing
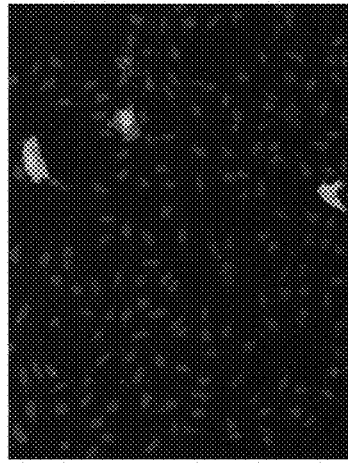
Control E, $AC_{50}$ = 195nM
*Example of image*
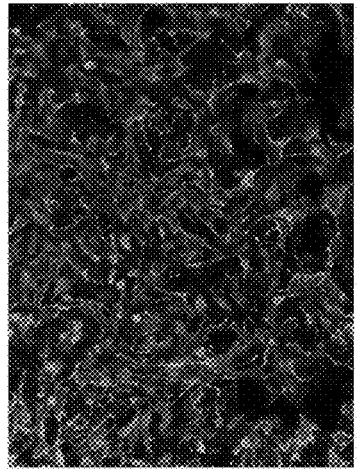
Infection + Buffer    Infection + 35ug/ml Ranpirnase

Figure 9
Ranpirnase in CHIV/U2OS

RAN = Ranpirnase (solution)

RAN = Ranpirnase (powder)

Figure 10
Results of QC testing in EBOV/HeLa

Control inhibitor E

Control E, $AC_{50}$ = 219-295nM

Robust statistics for the data on both days of testing

Example of image

Infection + 35 ug/ml Ranpirnase

Infection + Buffer

EBOV+RAN

Figure 11
Ranpirnase in EBOV/HeLa

RAN = Ranpirnase (solution)

RAN-2 = Ranpirnase (powder)

EBOV+RAN

% INH / % Viability

No toxic effect some toxic effect at 35ug/ml

| Compound ID | Plate ID | pAC50 ug/ml | Lower 95% CI | Upper 95% CI | Fit strategy | Fit Model | wRMSE (Y/Y) | R^2 | CC50 | SI |
|---|---|---|---|---|---|---|---|---|---|---|
| RAN | AA0800083672 | 5.60 | 4.53 | 6.37 | Smart Fit | 3p4HIII (AC50, n, S0) | 2.254263 | 0.992383 | >35 | >6.2 |
| RAN, rep2 | AA0800082013 | 4.73 | 4.17 | 5.42 | Smart Fit | 3p4HIII, ds (AC50, n, S0) | 2.082259 | 0.995214 | >35 | >7.4 |
| RAN-2 | AA0800083672 | 4.45 | 3.93 | 5.04 | Smart Fit | 3p4HIII (AC50, n, S0) | 2.765316 | 0.992194 | >35 | >7.9 |
| RAN-2, rep2 | AA0800082013 | 5.64 | 5.27 | 6.04 | Smart Fit | 3p4HIII (AC50, n, S0) | 2.05908 | 0.995288 | >35 | >6.2 |

Figure 12

EBOV+RAN

Results of QC testing in EBOV/Vero E6

Control inhibitor E

% INH

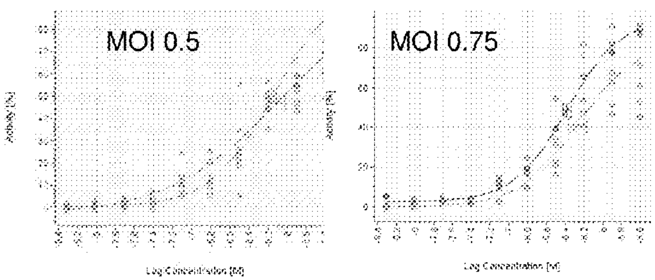

Control E, MOI 0.5, $AC_{50}$= 417-540nM,
Control E, MOI 0.75, $AC_{50}$= 721-778nM Robust statistics for the data on both days of testing

| Cells | MOI | Plate ID | Well Masking | Nuclei Number | % Infection | Z' Factor | Number of Analyzed Fields |
|---|---|---|---|---|---|---|---|
| VeroE6 | 0.5 | AA00002732 | 0% | 7160.5 | 93.110 | 0.914 | 5 |
| VeroE6 | 0.5 | AA00002009 | 0% | 6085 | 89.542 | 0.938 | 5 |
| VeroE6 | 0.75 | AA00002731 | 0% | 6908 | 93.339 | 0.958 | 5 |
| VeroE6 | 0.75 | AA00000375 | 0% | 5832 | 91.797 | 0.912 | 5 |

Example of image

Infection + Buffer

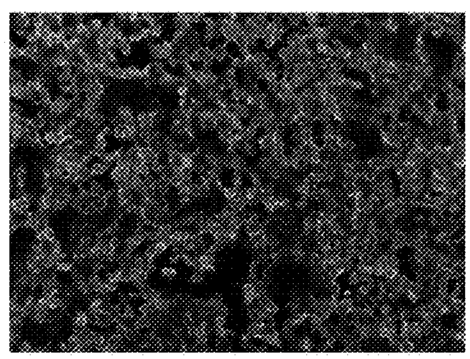

Infection+ 35 ug/ml Ranpirnase

Ranpirnase in EBOV/Vero E6

Figure 14: AC50 results for ranpirnase inhibition of VEEV, CHIV, and EBOV:

| Testing conditions | AC50 for ranpirnase |
|---|---|
| | |
| VEEV in primary astrocytes | 10-12 μg/ml with no detectable cytotoxic effect |
| VEEV in HeLa cells | 3.2-4.5 μg/ml with no detectable cytotoxic effect |
| CHIV in U2OS cells | 1.7-1.6 μg/ml and show some toxicity (<80% viability) at 35μg/ml |
| EBOV in HeLa cells | 0.5-0.73 μg/ml with no detectable cytotoxic effect |
| EBOV in Vero E6 | 4.7-5.6 μg/ml (some toxicity at 17.5μg/ml) |

Figure 15: Dose response study of ranpirnase in mice infected with EBOV:

| Group | N | Ranpirnase treatment (mg/kg) | Dose (mg/kg) | Dose volume (μL) | Dose concentration (mg/mL) |
|---|---|---|---|---|---|
| | | | | | |
| 1 | 10 | 0.9% saline control | – | 100 | – |
| 2 | 10 | 0.1 ranpirnase | 0.1 | 100 | 0.02 |
| 3 | 10 | 0.02 ranpirnase | 0.02 | 100 | 0.004 |
| 4 | 10 | 0.004 ranpirnase | 0.004 | 100 | 0.0008 |

Figure 16: Survival of mice infected with EBOV:

| Group | Treatment | Number of mice surviving on identified day post-infection | | | | | | | | | | | | |
|---|---|---|---|---|---|---|---|---|---|---|---|---|---|---|
| | | 0 | 1 | 2 | 3 | 4 | 5 | 6 | 7 | 8 | 9 | 10 | 11 | 12 |
| 1 | 0.9% saline control | 10 | 10 | 10 | 10 | 10 | 10 | 9 | 0 | 0 | 0 | 0 | 0 | 0 |
| 2 | 0.1 Ranpirnase | 10 | 10 | 10 | 10 | 10 | 10 | 10 | 9 | 7 | 7 | 7 | 7 | 7 |
| 3 | 0.02 Ranpirnase | 10 | 10 | 10 | 10 | 10 | 10 | 10 | 0 | 0 | 0 | 0 | 0 | 0 |
| 4 | 0.004 Ranpirnase | 10 | 10 | 10 | 10 | 10 | 10 | 8 | 3 | 1 | 1 | 1 | 1 | 1 |

Figure 18: Absolute Weight Loss of Mice Infected with EBOV:

| Group | Treatment | Total weight of mice living on identified day post-infection | | | | |

Figure 21: Ranpirnase inhibition of adenovirus in NHBE cells

| Infected | Test Material | Concentration | Number of Replicates |
|---|---|---|---|
| Yes | Ranpirnase | 50 µM | 6 |
| | | 10 µM | 6 |
| | | 5.0 µM | 6 |
| | | 1.0 µM | 6 |
| Yes | Cell culture medium = Placebo (Virus control) | | 3 |
| Yes | 2',3'-dideoxcytidine | 50 µg/ml | 1 |
| | | 16 µg/ml | 1 |
| | | 5 µg/ml | 1 |
| | | 1.6 µg/ml | 1 |
| | | 0.16 µg/ml | 1 |
| Sham | Ranpirnase | 50 µM | 1 |
| | | 10 µM | 1 |
| | | 5.0 µM | 1 |
| | | 1.0 µM | 1 |
| Sham | 2',3'-dideoxcytidine | 50 µg/ml | 1 |
| | | 16 µg/ml | 1 |
| | | 5 µg/ml | 1 |
| | | 1.6 µg/ml | 1 |
| | | 0.16 µg/ml | 1 |
| Sham | None (Cell control) | --- | 1 |

Figure 23: Ranpirnase inhibition of canine parvovirus in A-72 cells

| Ranpirnase concentration | Hemagglutination titer for virus diluted at: | | | | | |
|---|---|---|---|---|---|---|
| | Undiluted | 1/10 | 1/100 | 1/1,000 | 1/10,000 | No virus |
| 10 µg/ml | Neg | Neg | Neg | Neg | Neg | Neg |
| 5 µg/ml | Neg | Neg | Neg | Neg | Neg | Neg |
| 2.5 µg/ml | Neg | Neg | Neg | Neg | Neg | Neg |
| 1.25 µg/ml | Neg | Neg | Neg | Neg | Neg | Neg |
| 0.625 µg/ml | Neg | Neg | Neg | Neg | Neg | Neg |
| 0.3125 µg/ml | Neg | Neg | Neg | Neg | Neg | Neg |
| 0.15625 µg/ml | 640 | Neg | Neg | Neg | Neg | Neg |
| No Ranpirnase (control) | 640 | 640 | 320 | Neg | Neg | Neg |

Figure 24: Ranpirnase inhibition of respiratory syncytial virus in NHBE cells

| Infected | Test Material | Concentration | Number of Replicates |
|---|---|---|---|
| Yes | Ranpirnase | 5 µM | 5 |
| | | 0.5 µM | 5 |
| | | 0.1 µM | 5 |
| Yes | Cell culture medium = Placebo (Virus control) | 0.5 µg/ml | 2 |
| Sham | Ranpirnase (toxicity control) | 5 µM | 3 |
| | | 0.5 µM | 3 |
| | | 0.1 µM | 3 |
| Sham | None (cell control) | -- | 1 |

Figure 26: Ranpirnase inhibition of rhinovirus-14 in NHBE Cells

| Infected | Test Material | Concentration | Number of Replicates |
|---|---|---|---|
| Yes | Ranpirnase | 50 µM | 6 |
|  |  | 10 µM | 6 |
|  |  | 5.0 µM | 6 |
|  |  | 1.0 µM | 6 |
| Yes | Cell culture medium = Placebo (Virus control) |  | 3 |
| Yes | pirodavir | 10 µg/ml | 1 |
|  |  | 3.2 µg/ml | 1 |
|  |  | 1.0 µg/ml | 1 |
|  |  | 0.32 µg/ml | 1 |
|  |  | 0.1 µg/m | 1 |
|  |  | 0.032 µg/ml | 1 |
| Sham | Ranpirnase | 50 µM | 1 |
|  |  | 10 µM | 1 |
|  |  | 5.0 µM | 1 |
|  |  | 1.0 µM | 1 |
| Sham | pirodavir | 10 µg/ml | 1 |
|  |  | 3.2 µg/ml | 1 |
|  |  | 1.0 µg/ml | 1 |
|  |  | 0.32 µg/ml | 1 |
|  |  | 0.1 µg/m | 1 |
|  |  | 0.032 µg/ml | 1 |
| Sham | None (Cell control) | --- | 3 |

Figure 28: Ranpirnase inhibition of vaccinia in Vero 76 cells

| Infected | Test Material | Concentration | Number of Replicates |
|---|---|---|---|
| Yes | Ranpirnase | 50 µM | 2 |
| | | 16 µM | 2 |
| | | 5.0 µM | 2 |
| | | 1.6 µM | 2 |
| | | 0.5 µM | 2 |
| | | 0.16 µM | 2 |
| | | 0.05 µM | 2 |
| Yes | Cell culture medium = Placebo (Virus control) | | 2 |
| Yes | cidofovir | 100 µM | 2 |
| | | 32 µM | 2 |
| | | 10 µM | 2 |
| | | 3.2 µM | 2 |
| | | 1.0 µM | 2 |
| | | 0.32 µM | 2 |
| | | 0.1 µM | 2 |
| Sham | Ranpirnase | 50 µM | 2 |
| | | 16 µM | 2 |
| | | 5.0 µM | 2 |
| | | 1.6 µM | 2 |
| | | 0.5 µM | 2 |
| | | 0.16 µM | 2 |
| | | 0.05 µM | 2 |
| Sham | cidofovir | 100 µM | 2 |
| | | 32 µM | 2 |
| | | 10 µM | 2 |
| | | 3.2 µM | 2 |
| | | 1.0 µM | 2 |
| | | 0.32 µM | 2 |
| | | 0.1 µM | 2 |
| Sham | None (Cell control) | --- | 2 |

Figure 29: Ranpirnase inhibition of vaccinia in Vero 76 cells

Virus: Vaccinia
Cells: African green monkey kidney cells (Vero 76)
Assay: Plaque Assay

| | |
|---|---:|
| EXPT. # | TAM/VAC-1 |
| COMPOUND # | Ranpirnase (µM) |
| CC50: | >100 |
| EC50: | 3.8 |
| SI: | >26 |
| COMMENT: | Very active. |

| | |
|---|---:|
| EXPT. # | TAM/VAC-2 |
| COMPOUND # | Cidofovir (µM) |
| CC50: | >100 |
| EC50: | 10 |
| SI: | >10 |
| | Active as expected. |

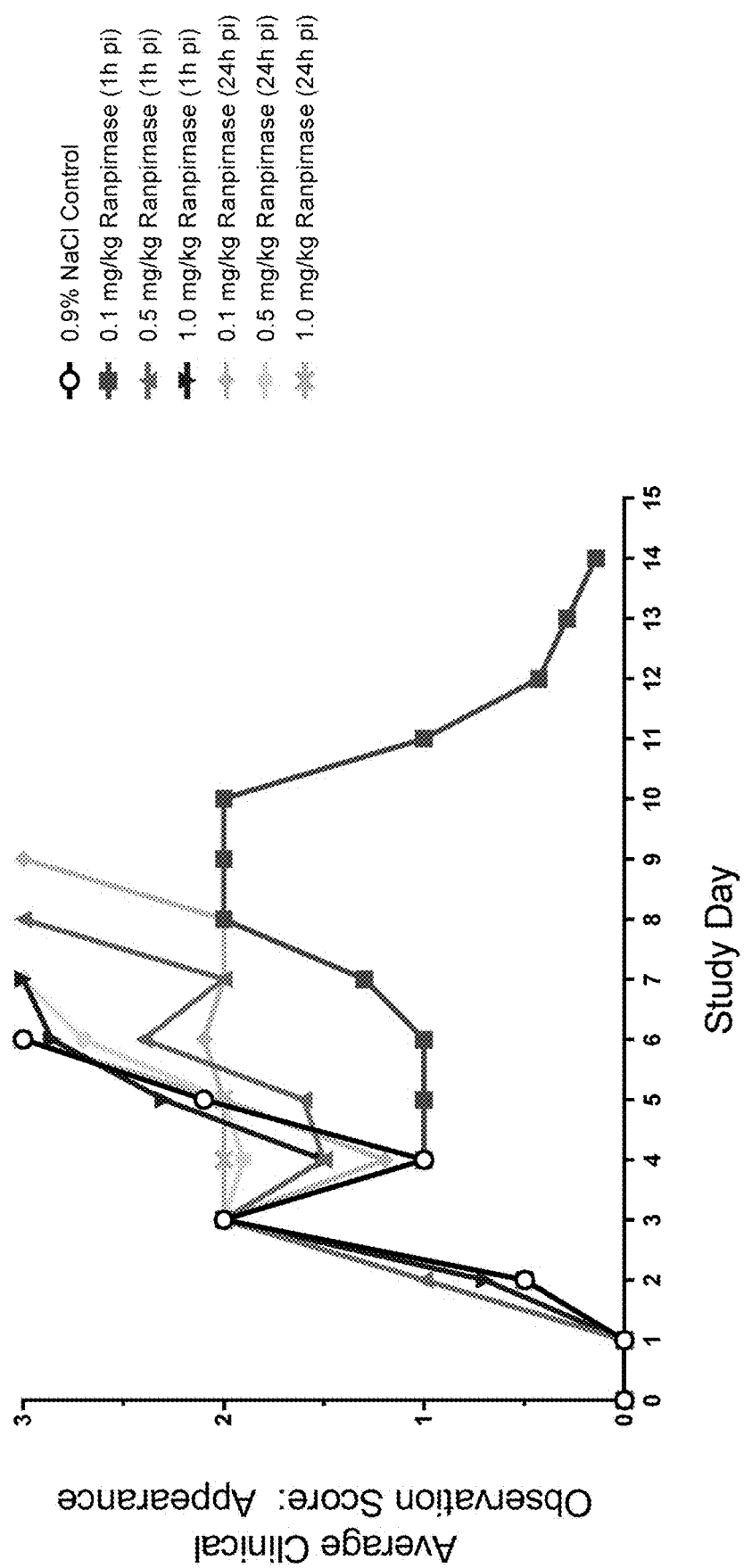

METHODS OF TREATING AND PROPHYLACTICALLY PROTECTING MAMMALIAN PATIENTS INFECTED BY VIRUSES CLASSIFIED IN BALTIMORE GROUP V

BACKGROUND OF THE INVENTION

The invention relates to treatment of viral infections, and more particularly relates to treatment of viral infections in mammalian patients. In its most immediate sense, the invention relates to treatment of rabies, Middle East Respiratory Syndrome Coronavirus ("MERS-CoV"), influenza, Ebola virus ("EBOV"), Chikungunya virus ("CHIV"), Venezuelan equine encephalitis ("VEEV"), canine parvovirus, adenovirus ("AV"), respiratory syncytial virus ("RSV"), rhinovirus ("RV"), and poxvirus.

Various drugs, including ranpirnase, have been proposed as anti-viral agents. However, the demonstrated activity of each of these drugs has been specific to one or only a few particular viruses.

SUMMARY OF THE INVENTION

Recent experiments have shown that ranpirnase demonstrates surprisingly strong antiviral effects against a surprisingly large number of different viruses, including viruses (e.g. MERS-CoV and EBOV) that are highly resistant to treatment.

It is believed that the surprisingly broad-spectrum activity of the invention comes from the ways in which ranpirnase degrades various forms of RNA. To date, three RNA-degrading mechanisms appear to be relevant to antiviral therapy using ranpirnase.

The first of these mechanisms is degradation of tRNA. Degrading tRNA inside a mammalian cell makes that cell resistant to some viral infections. This is because some viruses replicate by protein synthesis using the ribosome, and protein synthesis cannot occur unless transfer RNAs enter the ribosome to deliver the amino acids needed to synthesize the protein. Thus, a systemic application of an agent that degrades tRNA will prevent or at least substantially impede some viruses from spreading to uninfected cells. If this application occurs before the virus has spread widely enough to endanger the host mammal, the virus will eventually die.

The second mechanism is degradation of viral double-stranded RNA. Some viruses produce double-stranded RNA as part of their process of proliferation in mammalian cells, and destroying that double-stranded RNA can prevent or at least substantially impede replication of such viruses.

The third mechanism is degradation of microRNA and siRNA. In certain viruses that proliferate using double-stranded RNA, that double-stranded RNA is produced by the interaction of microRNA or siRNA with single-stranded RNA. Destroying the microRNA or siRNA can prevent the formation of the viral double-stranded RNA by which the virus replicates.

Ranpirnase is known to degrade each of these RNAs. It degrades tRNA very effectively (see Lin et al., *Biochemical and Biophysical Research Communications* 201(1), 156-162 (1994)). And, because normal mammalian cells degrade approximately 80% of their tRNA as a natural process, this degradation causes little if any harm to the cells themselves. As a result, except in instances where a viral infection has spread too far to be effectively controlled, a systemic application of ranpirnase causes some viruses to die out without killing the normal cells that those viruses infect.

Ranpirnase is known to degrade double-stranded RNA as well (see Saxena et al., *Anticancer Res.* 29(4), 1067-1071 (April 2009)). And, ranpirnase is known to degrade certain microRNA (see Goparaju et al., *Oncogene* 30(24), 2767-2777, (Jun. 16, 2011)) and certain siRNA (see Zhao et al., *Cell Cycle.* 7(20), 3258-3261 (October 2008)).

Hence, it appears that the RNA-degrading characteristics of ranpirnase make it possible to use ranpirnase as a pharmaceutical for treating a wide variety of viral infections in mammals by administering ranpirnase systemically. And, it also appears that these characteristics permit ranpirnase to be administered prophylactically as well as therapeutically.

Furthermore, it is believed that other ribonucleases will have the same antiviral effects that ranpirnase has. These other ribonucleases (including the below-identified "'805 variant", "Amphinase 2", and rAmphinase 2") are highly homologous to ranpirnase and have exhibited antiviral properties that are highly similar to those of ranpirnase when treating other viral infections.

BRIEF DESCRIPTION OF THE DRAWINGS

In the drawings, wherein $CC_{50}$ is the cytotoxic concentration (expressed in nM) of ranpirnase, i.e. the ranpirnase concentration that decreased cell viability by 50%, and $IC_{50}$ is the inhibitory concentration (expressed in nM) of ranpirnase, i.e. the ranpirnase concentration that inhibited replication of the virus under test by 50%, SI, the selective index, is $CC_{50}/IC_{50}$. The higher the value of SI, the more active is the ranpirnase against the virus under test, FIG. 1 shows the results of testing the anti-viral activity of ranpirnase against rabies virus in three separate cell lines;

FIG. 2 shows the results of testing the anti-viral activity of various concentrations of ranpirnase against MERS-CoV virus in normal human bronchial epithelial ("NHBE") cells, compared with the anti-viral activities of various concentrations of SARS protease inhibitor and Infergen;

FIG. 4 shows results of quality control (QC) testing of ranpirnase against VEEV infection in astroctyes;

FIG. 6 shows results of QC testing of ranpirnase against VEEV infection in HeLa cells;

FIG. 7 shows the effect of ranpirnase against VEEV infection in HeLa cells;

FIG. 8 shows results of QC testing of ranpirnase against CHIV infection in U2OS cells;

FIG. 9 shows the effect of ranpirnase against CHIV infection in U2OS cells;

FIG. 10 shows results of QC testing of ranpirnase against EBOV infection in HeLa cells;

FIG. 11 shows the effect of ranpirnase against EBOV infection in HeLa cells;

FIG. 12 shows results of QC testing of ranpirnase against EBOV infection in Vero E6 cells;

FIG. 14 shows the AC50 toxicity values for ranpirnase inhibition of VEEV, CHIV, and EBOV;

FIG. 15 shows the doses used in a dose response study of prophylactically administered ranpirnase in mice infected with EBOV;

FIG. 16 shows mouse survival in the study of FIG. 15;

FIG. 18 shows mouse weight loss in the study of FIG. 15;

FIG. 19 shows mouse weight loss in the study of FIG. 15 in percentage terms;

FIG. 21 shows the doses of ranpirnase used in a study of ranpirnase inhibition of AV in NHBE cells;

FIG. 23 shows the results of a study of ranpirnase inhibition of canine parvovirus in A-72 cells;

FIG. 24 shows the doses of ranpirnase used in a study of ranpirnase inhibition of RSV in NHBE cells;

FIG. 26 shows the doses of ranpirnase used in a study of ranpirnase inhibition of RV-14 in NHBE cells;

FIG. 28 shows the doses of ranpirnase used in a study of ranpirnase inhibition of vaccinia in Vero 76 cells;

FIG. 29 shows the results of the study of FIG. 28;

FIG. 34 is a graph showing variation in the appearance of Ebola-infected BALB/c mice in the tested groups during the experiment.

DETAILED DESCRIPTION OF PREFERRED EMBODIMENTS

Figure 3:
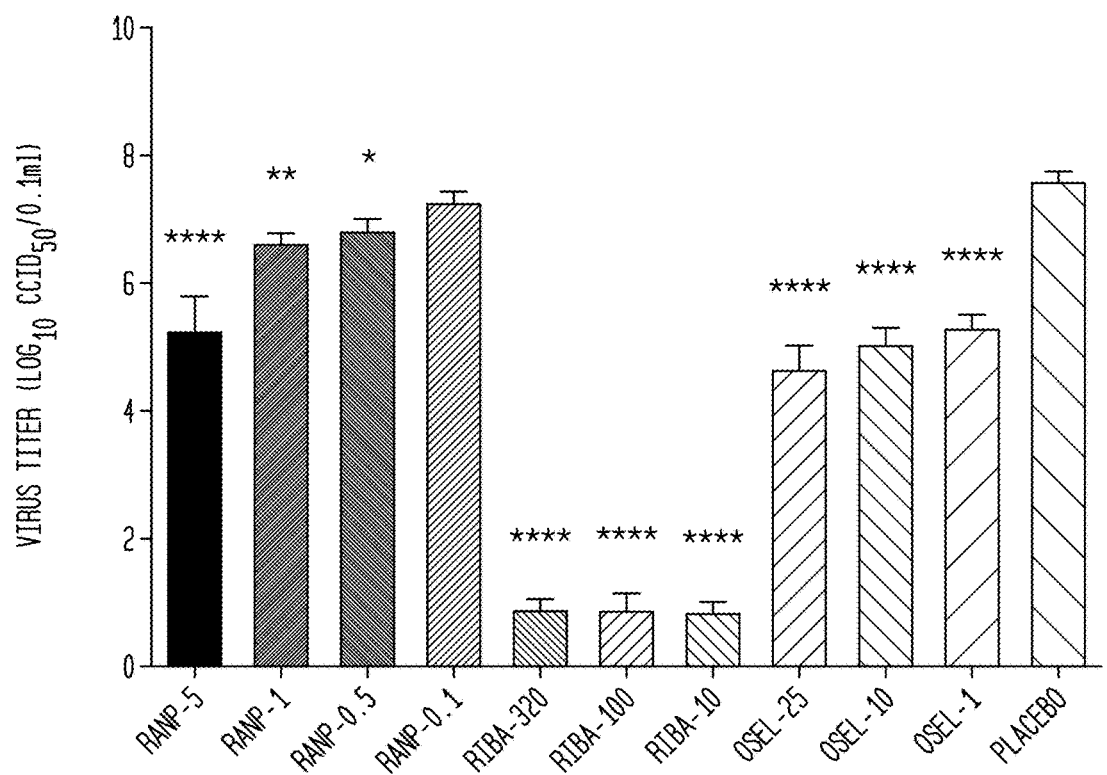
FIG. 3 shows the results of testing the anti-viral activity of various concentrations of ranpirnase ("Ranp") against a strain of influenza in NHBE cells, compared with the anti-viral activities of various concentrations of Ribavirin ("Riba") and Oseltamivir carboxylate ("Osel")

Example 1: Rabies in MEM, EF, and BSR Cells

In the experiments described in FIG. 1, the density of each of the cell lines under test was adjusted to 50,000 cells/ml using minimal essential media (MEM). The cells were placed in wells and incubated at 37° C. and 0.5% $CO_2$ for 24 hours. Ranpirnase was diluted to concentrations of 10 uM, 3 uM, 900 nM, 270 nM, 81 nM, and 24 nM, added to the wells, and incubated at 37° C. and 0.5% $CO_2$ for 24 hours.

Rabies virus at a multiplicity of infection ("MOI") of 0.1 was then added to each of the wells and the ranpirnase and rabies virus—containing wells were incubated at 37° C. and 0.5% $CO_2$ for 72 hours.

The virus in each of the wells was titrated 24 and 48 hours after introduction of the rabies virus using mouse neuroblastoma cells, and the results are shown in FIG. 1.

The selectivity index SI is an accepted measurement of the ability of a drug under test to inhibit replication of a viral infection without killing the infected cells. Where SI in the accompanying Figure is greater than 1, ranpirnase is active against the virus indicated, and increasing values of SI indicate increasing activity. Thus, as can be seen in FIG. 1 at 24 hours after introduction of viruses into ranpirnase-containing cell lines, ranpirnase is extraordinarily active against rabies in the mammalian cell lines indicated.

Because SI measures the ability of a substance under test to inhibit replication of a particular virus without killing the infected cells themselves, it is reasonably correlated with usefulness of the substance in treating a mammalian subject that is infected with the virus. Accordingly, test results in which SI>1 indicate that mammalian subjects infected with rabies can be treated by systemic administration of an appropriate dose of ranpirnase. Furthermore, other below-disclosed experimental results in VEEV, CHIV, and EBOV indicate that it should be possible to use ranpirnase as a prophylactic to prevent rabies infection.

Example 2: MERS-CoV in NHBE Cells

In the experiment illustrated in FIG. 2, the anti-viral activity of ranpirnase against MERS-CoV virus was compared to the activities of two known anti-viral agents: SARS protease inhibitor and Infergen. The experiment was carried out using four different concentrations of each agent on normal human bronchial epithelial (NHBE) cells.

More specifically, the NHBE cells were grown in HEPES Buffered Saline Solution at 37° C. for seven days. The cells were washed and refreshed once daily. Two controls were used: one contained MERS-CoV virus and the other contained uninfected NHBE cells that were treated with the agents under test.

On the eighth day, the tested concentrations of the three agents under test were introduced into the cells and buffer solution and the virus was introduced at a multiplicity of infection ("MOI") of 0.01. The virus- and agent-containing samples were then incubated for 72 hours at 37° C. and 5% $CO_2$, with the medium being replenished once each day. After 72 hours, the samples were then titrated to determine their viral content.

In this experiment SI was not calculated. Rather, the anti-viral activity of the various agents under test was determined by comparing viral production (viral titer in Vero 76 cells) in NHBE cells that had been treated with the various agents under test to the viral production in the NHBE cells used as controls.

As can be seen in FIG. 2, ranpirnase was far more active against MERS-CoV virus than either of the other agents. And, the activity of ranpirnase was clearly statistically significant, since all but the least concentrated of the doses of ranpirnase had a p value of less than 0.0001. This reduction of viral titers of MERS-CoV virus without killing the host cells is reasonably correlated with usefulness of ranpirnase in treating MERS-CoV.

Because ranpirnase was so effective at inhibiting replication of the MERS-CoV virus in NHBE cells while not killing the host cells, this experiment further evidences the likelihood that systemically administered ranpirnase will be useful in treating a mammalian subject infected with a virus, and particularly a mammalian subject infected with MERS-CoV virus. Furthermore, other below-disclosed experimental results in VEEV, CHIV, and EBOV indicate that it should be possible to use ranpirnase as a prophylactic to prevent MERS-CoV infection.

Example 3: Influenza in NHBE Cells

In the experiment illustrated in FIG. 3, the anti-viral activity of various concentrations (5 μg/ml "Ranp-5", 1

µg/ml "Ranp-1", 0.5 µg/ml "Ranp-0.5", and 0.1 µg/ml "Ranp-0.5") of ranpirnase against influenza A/California/07/2009(H1N1)pdm09 virus was compared to the activities of various concentrations of two known anti-viral agents (Ribavirin at 320 µg/ml "Riba-320", 100 µg/ml "Riba-100", and 10 µg/ml "Riba-20" and Oseltamivir carboxylate at 25 µM "Osel-25", 10 µM "Osel-10", and 1 µM) "Osel-1". The experiment was carried out on NHBE cells using four different concentrations of ranpirnase and three different concentrations of each of the other agents. Three controls were used. The first control was NHBE cells that were infected by the virus and treated with a placebo. (This control is shown in FIG. 3.) The second control was NHBE cells that were "infected" with a placebo and treated using the agents under test. The third control was NHBE cells that were "infected" with a placebo and treated with a placebo.

The NHBE cells were supplied with the vendor's proprietary culture medium and equilibrated at 37° C. and 5% $CO_2$ for at least 16 hours. After equilibration, the cells were washed and refreshed.

NHBE cells were then infected with influenza A/California/07/2009(H1N1)pdm09 virus at a multiplicity of infection level of 0.01. After an adsorption period of 1 hour, the viral inoculum was removed and the treatments were applied. Twenty four hours post infection, the treatments were replenished. Forty eight hours post infection, the supernatants were harvested. Then, virus titers were determined in Madin-Darby-Canine-Kidney cells and analyzed for statistical significance using one-way analysis of variance.

As can be seen in FIG. 3, with the exception of the least concentrated dose, the activity of ranpirnase against influenza A/California/07/2009(H1N1)pdm09 virus was statistically significant and dose-dependent. And, these experiments confirmed a result that was seen in the experiment illustrated in FIG. 2: ranpirnase did not decrease the viability of NHBE cells at any of the concentrations under test.

This reduction of viral titers of influenza A/California/07/2009(H1N1)pdm09 virus without reduction of viability of the host cells is reasonably correlated with usefulness of ranpirnase in treating influenza A/California/07/2009 (H1N1)pdm09. Because ranpirnase inhibited replication of the tested influenza virus in NHBE cells while not killing the cells themselves, this experiment further evidences the likelihood that systemically administered ranpirnase will be useful in treating a mammalian subject infected with a virus, and particularly a mammalian subject infected with influenza. Furthermore, other below-disclosed experimental results in VEEV, CHIV, and EBOV indicate that it should be possible to use ranpirnase as a prophylactic to prevent influenza infection.

Example 4: VEEV, CHIV, and EBOV (all In Vitro)

Methodology

Several studies were conducted to assess the ability of ranpirnase to inhibit infection of cells by VEEV, CHIV, and EBOV. Ranpirnase solution and powder-derived ranpirnase were tested. The powder-derived ranpirnase was lyophilized ranpirnase provided by Tamir Biotechnology, Inc. Quality control of the assay was conducted using Positive (Neutral) control (n=16) or infected cells+media, uninfected cells (Negative control) (n=16) and dose response for control inhibitors (n=2 or 4). Z' was calculated for Neutral control and uninfected cells. Data were normalized on the plate bases. Data analysis was done using GeneData software and analysis of dose response curve to determine ED50 of ranpirnase was performed using GeneDataCondoseo software applying Levenberg-Marquardt algorithm (LMA) for curve fitting strategy.

VEEV in Astrocytes

Figure 5:
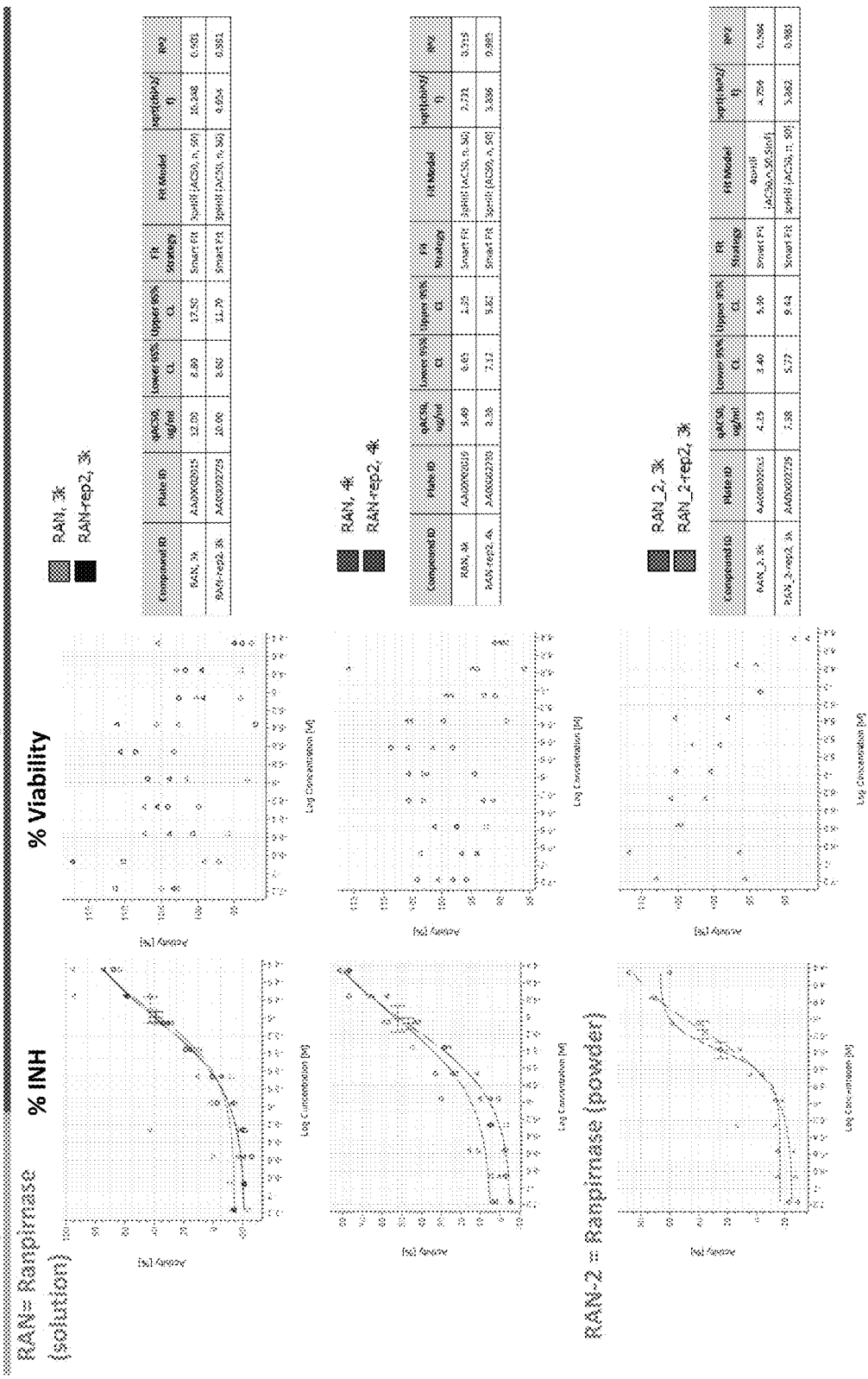
FIG. 5 shows the effect of ranpirnase against VEEV infection in astrocytes.

To test the effect of ranpirnase on VEEV infection of astrocytes, ranpirnase solution ("RAN") was tested in duplicated 10 point dose response, and powder-derived ranpirnase ("RAN-2") was re-suspended in phosphate buffered saline at 3.5 mg/ml and was tested only as a single dose response. Both the RAN and the RAN-2 were tested in two independent experiments. In these experiments, astrocytes were plated at 4,000 and 3,000 cells/well, incubated overnight and pre-treated with ranpirnase for 2 hours before the infection. Cells were infected at a multiplicity of infection ("MOI") equal to 0.05 for 20 hours. The results of the study are provided in FIGS. 4 and 5.

To test the effect of ranpirnase on VEEV infection of HeLa cells, RAN was tested in quadruplicated (n=4) 10 point dose response repeated in two independent experiments (rep1 and rep2). RAN2 was tested in n=2 dose responses on plate and repeated in 2 independent experiments. HeLa cells were plated at 4,000 cells/well, incubated overnight and pre-treated with ranpirnase 2 hours before infection. Cells were infected at an MOI equal to 0.05 for 20 hours. The results of the study are provided in FIGS. 6 and 7. As shown in FIG. 7, SI values were over 10 for RAN and over 7.75 for RAN-2.

CHIV in U2OS Cells

To test the effect of ranpirnase on CHIV infection of U2OS cells, ranpirnase solution was tested in quadruplicated (n=4) 10 point dose response repeated in two independent experiments (rep1 and rep2). The RAN2 stock was tested in n=2 dose responses on plate and repeated in two independent experiments. U2OS cells were plated at 3,000 cells/well, incubated overnight and pre-treated with ranpirnase 2 hours before infection. Cells were infected at a MOI equal to 0.4 for 24 hours. The results of the study are provided in FIGS. 8 and 9. As shown in FIG. 9, SI values were over 18.

EBOV in HeLa and Vero E6 Cells

Figure 13:
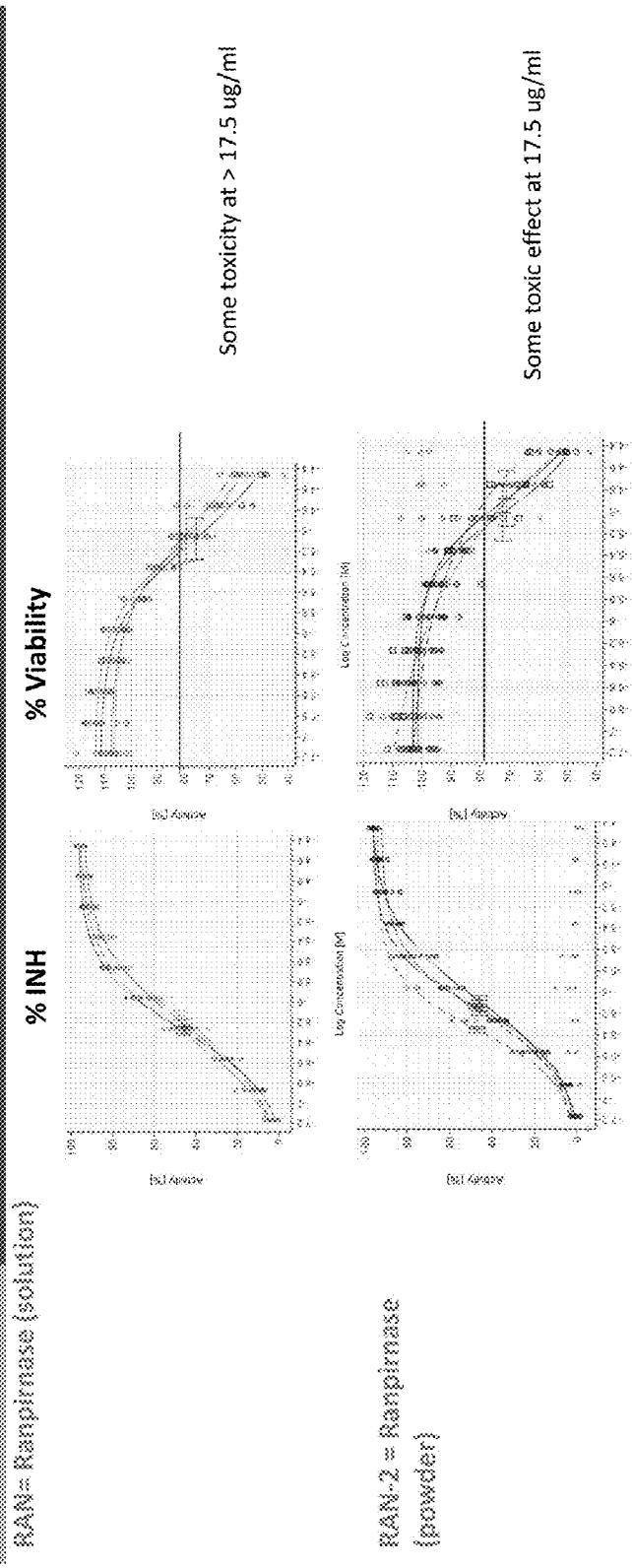
FIG. 13 shows the effect of ranpirnase against EBOV infection

To test the effect of ranpirnase on EBOV infection of HeLa and Vero E6 cells, ranpirnase solution was tested in quadruplicated (n=4) 10 point dose response repeated in two independent experiments (rep1 and rep2). The RAN2 stock was tested in n=2 dose responses on plate and repeated in two independent experiments. HeLa cells were plated at 4,000 cells/well and Vero E6 at 4000 cells/well, incubated overnight and pre-treated with ranpirnase 2 hours before infection. HeLa cells were infected at a MOI equal to 0.5 and Vero E6 cells were infected at a MOI equal to 0.5 and 0.75 for 48 hours. The results of the study are provided in FIGS. 10, and 11 (HeLa cells) and in FIGS. 12, and 13 (Vero E6 cells). SI values were unexpectedly high, ranging from over 40 to over 77 in Vero E6 cells (FIG. 13).

Summary of In Vitro VEEV, CHIV, and EBOV Experiments

The results of the study showed that ranpirnase exhibited robust inhibition of VEEV, CHIV, and EBOV, with surprisingly low AC50 values and surprisingly high SI values. Because SI measures the ability of a substance under test to inhibit replication of a particular virus without killing the infected cells themselves, it is reasonably correlated with usefulness of the substance in treating a mammalian subject that is infected with the virus. Accordingly, test results such as these in which SI>1 indicate that mammalian subjects infected with VEEV, CHIV, and EBOV can be treated by systemic administration of an appropriate dose of ranpirnase. FIG. 14 provides an overall summary of the AC50 results of the studies. AC50 indicates the concentration of the tested agent—here, ranpirnase—that produce half the maximum inhibition of the virus being inhibited.

These experiments demonstrate that ranpirnase inhibited replication of the tested VEEV, CHIV, and EBOV in various mammalian cells (astrocytes, HeLa cells, U2OS cells, Vero E6 cells) without killing the cells themselves. These experiments further evidence the likelihood that systemically administered ranpirnase will be useful in treating a mammalian subject infected with a virus, and particularly a mammalian subject infected with VEEV, CHIV, and EBOV. Furthermore, it is to be noted that in these experiments, the ranpirnase was used prophylactically, in that the viruses were introduced into cells that had already been treated with ranpirnase. These experiments therefore constitute evidence that the antiviral qualities of ranpirnase can be used prophylactically as well as therapeutically.

Example 5A: EBOV in Mice (Prophylactic Administration)

The effect of a range of prophylactically administered doses of ranpirnase in EBOV infected mice was studied. C57BL/6 mice (eight to twelve weeks old) were infected with 1000 PFU of mouse-adapted EBOV-Zaire. Infection was accomplished by intraperitoneal injection (intravenous tail vein infusion). 1 hour before infection, each mouse received 0.9% saline (control group; Group 1), 0.1 mg/kg ranpirnase (Group 2), 0.02 mg/kg ranpirnase (Group 3), or 0.004 mg/kg ranpirnase (Group 4). The study groups are shown in FIG. 15.

Figure 17:
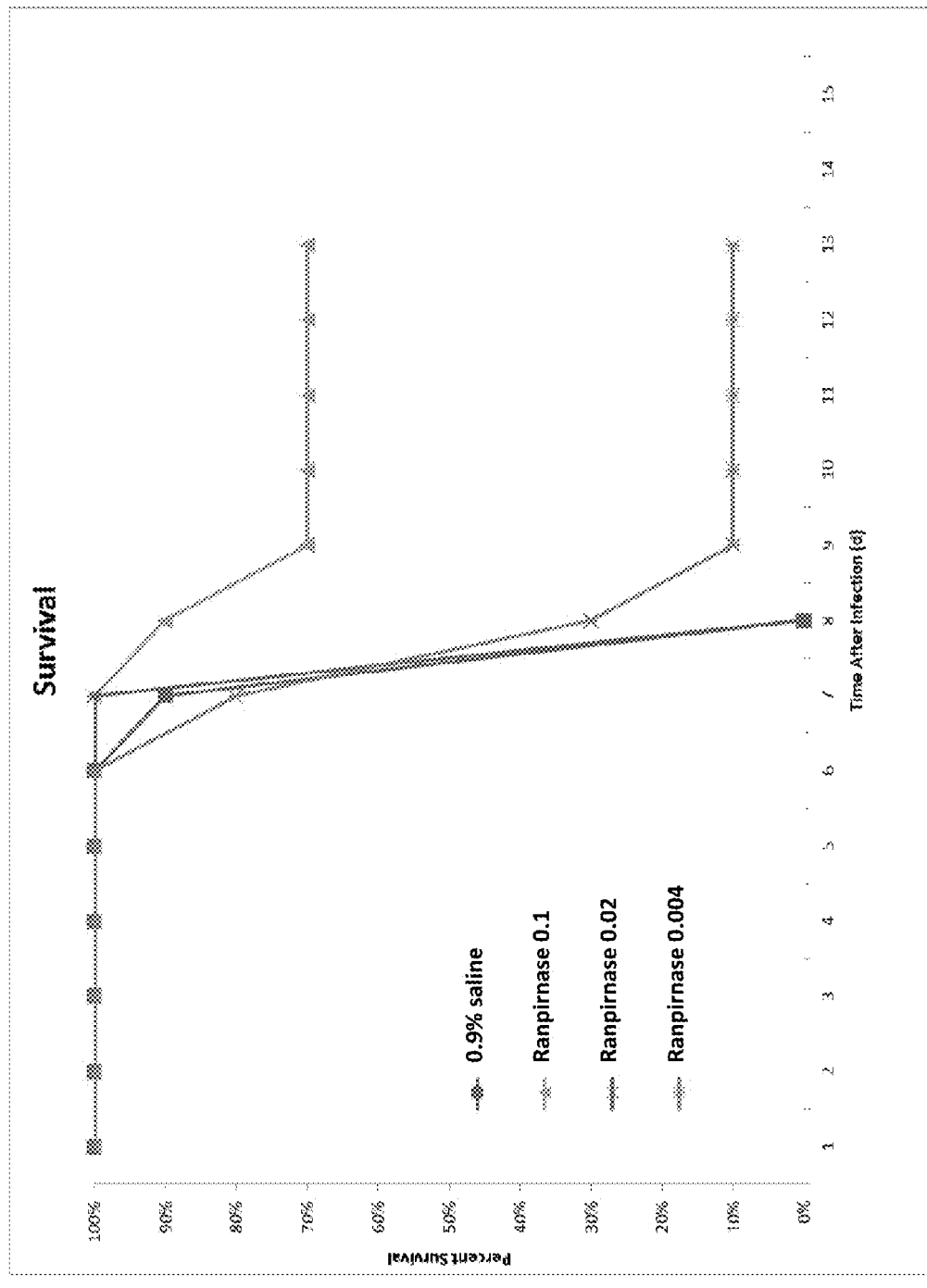
FIG. 17 is a graphical representation of the data in FIG. 16, shown in percentage terms.
Figure 18:
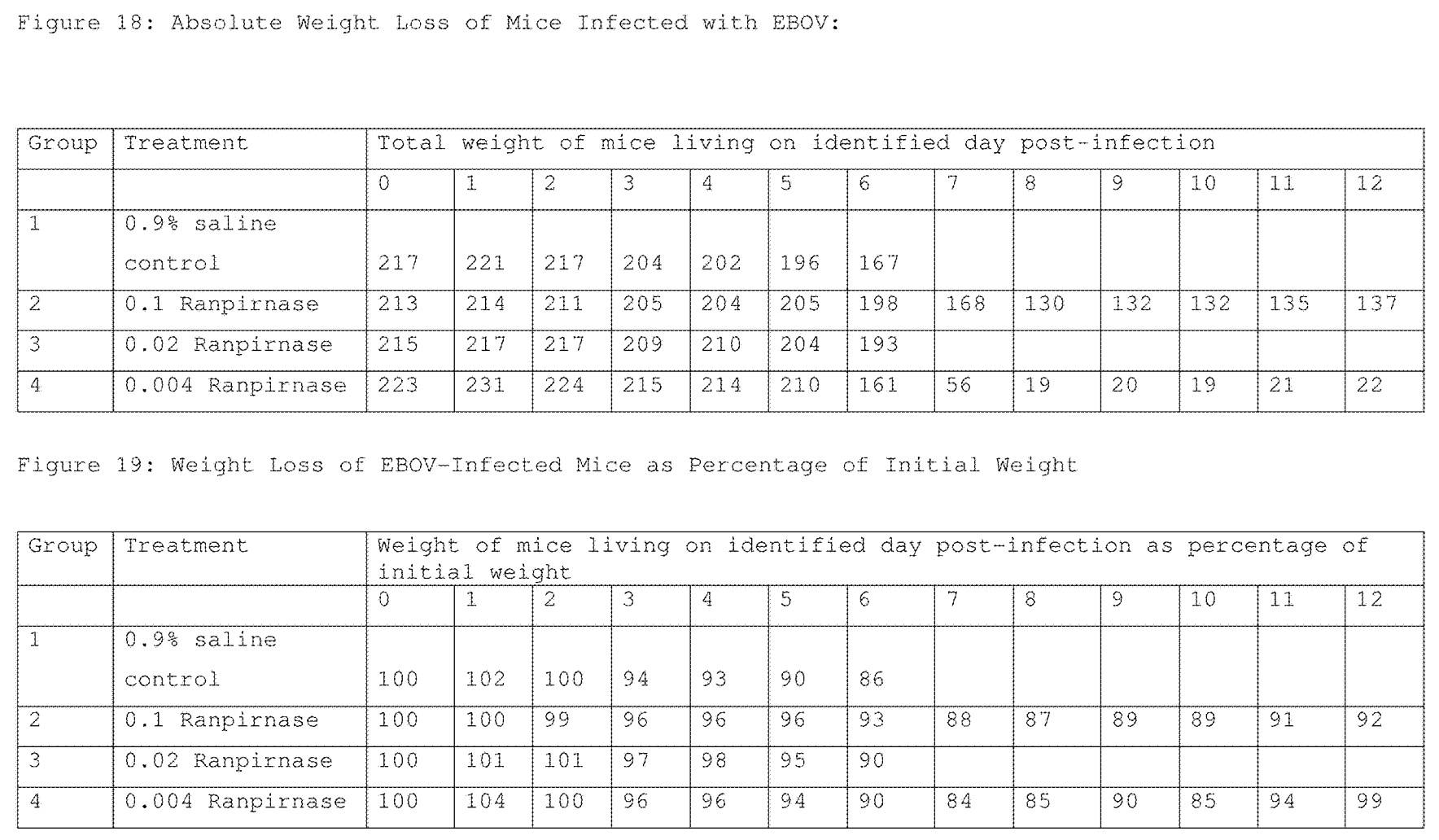
Figure 20:
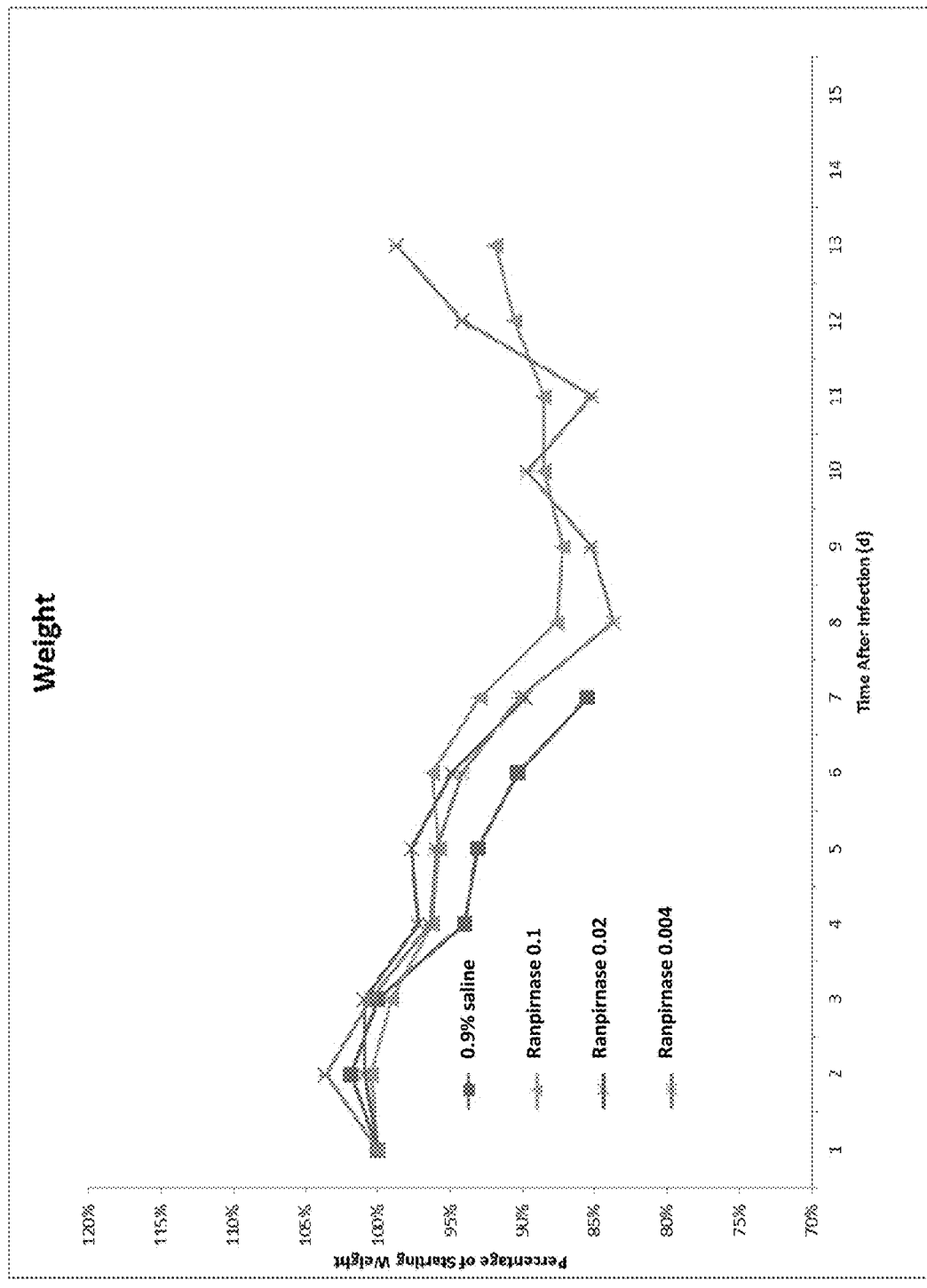
FIG. 20 is a graphical representation of the data in FIG. 19.

Mice were monitored for survival, and the weight of each mouse was obtained on the day of infection and every day for 14 days post infection. (FIGS. 16 and 17 show data for 12 days post infection, but monitoring of the mice continued for two additional days.) The number of survivors per group (out of 10 mice per group) and the percent survival in each group are provided in FIG. 16 and FIG. 17, respectively. The weight of the mice in each group and the percent change from the starting weight are shown below in FIGS. 18 and 19, respectively. The data in FIG. 19 are also shown in graphical form in FIG. 20.

The study showed that prophylactically administered ranpirnase provides protection from lethal Ebola virus infection in mice. In particular, at a dose of 0.1 mg/kg ranpirnase, 70% of mice survived for at least 14 days after infection. In comparison, in control mice that did not receive ranpirnase, Ebola virus infection was 100% lethal by 7 days post-infection. In addition, surviving mice in the 0.1 mg/kg ranpirnase group maintained a weight within 92% of their starting weight at 12 days post-infection. Thus, the study showed that prophylactically administered ranpirnase effectively promotes survival in Ebola virus infected mice. Animal testing showing such extended survival shows that ranpirnase treatment is reasonably correlated with usefulness in treating Ebola virus. This still further evidences the likelihood that systemically administered ranpirnase will be useful in treating a mammalian subject infected with a virus, and particularly a mammalian subject infected with Ebola virus. Furthermore, this result is consistent with the above-described experimental results in VEEV, CHIV, and EBOV, which indicate that it is possible to use ranpirnase as a prophylactic to prevent EBOV infection.

Example 5B: EBOV in Mice (Therapeutic Administration)

The therapeutic effect of a range of doses of ranpirnase in mice infected with Ebola virus was studied. BALB/c mice were infected with a target of 100 PFU of mouse-adapted EBOV-Mayinga-CDC-808012. Infection was accomplished by intraperitoneal injection.

Seven groups of mice were used. Each group contained five males and five females. In the control group, EBOV-infected mice received an intraperitoneal injection of 0.9% NaCl. EVOV-infected mice in the other groups received therapeutic doses of ranpirnase as follows:

Group 2: received 0.1 mg/kg ranpirnase 1 hour post-infection;

Group 3: received 0.5 mg/kg ranpirnase 1 hour post-infection;

Group 4 received 1.0 mg/kg ranpirnase 1 hour post-infection;

Group 5: received 0.1 mg/kg ranpirnase 24 hours post-infection;

Group 6: received 0.5 mg/kg ranpirnase 24 hours post-infection; and

Group 7 received 1.0 mg/kg ranpirnase 24 hours post-infection.

In each case, ranpirnase in the stated dose was administered twice per day for the first three days of the study and then once per day through Day 9. Mice remained on study until they died or until they were euthanized because they had lost more than 20% of their body weight.

Figure 30:
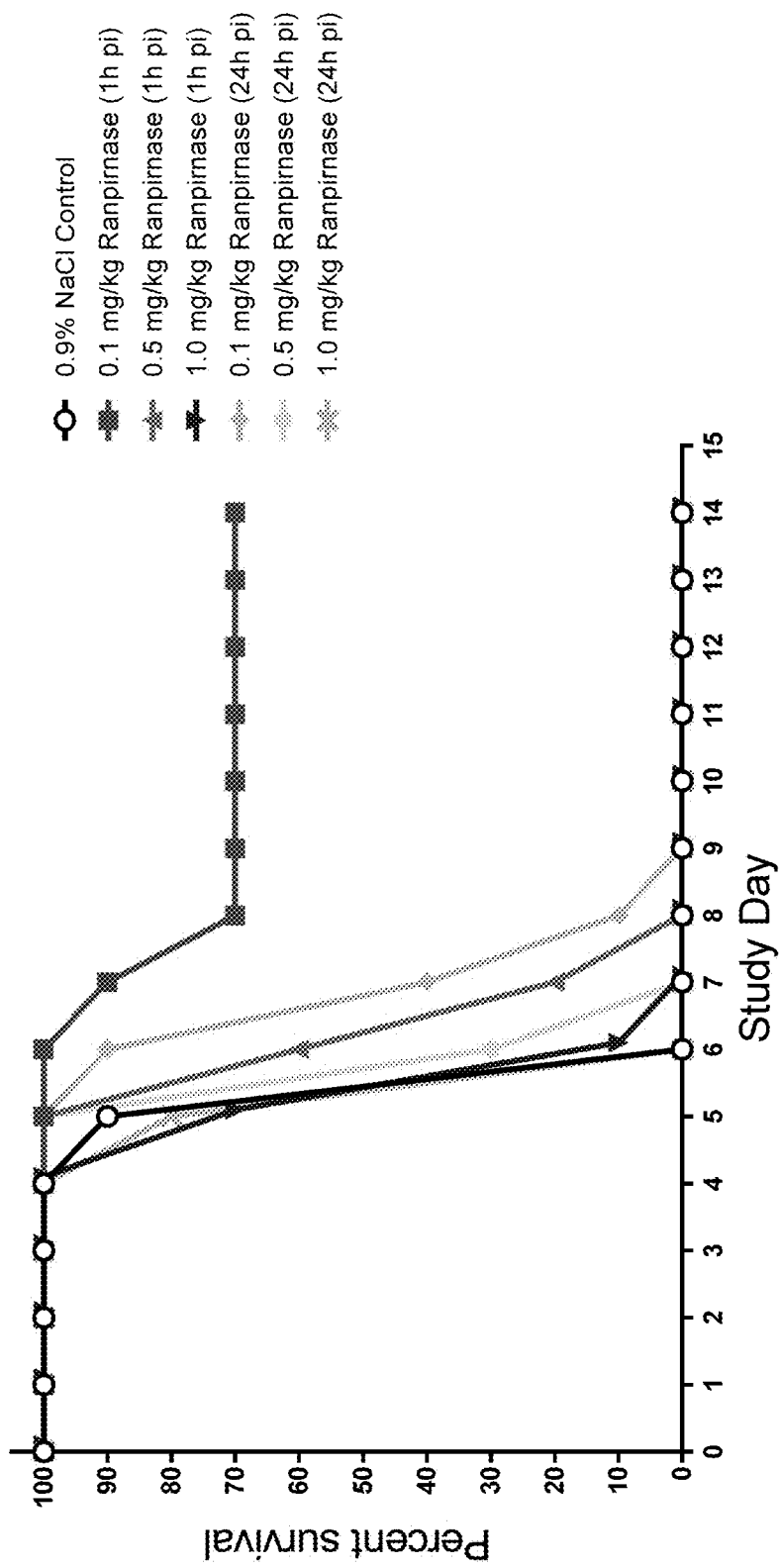
FIG. 30 is a graph showing survival of groups of Ebola-infected BALB/c mice that were therapeutically treated with ranpirnase.
Figure 31:
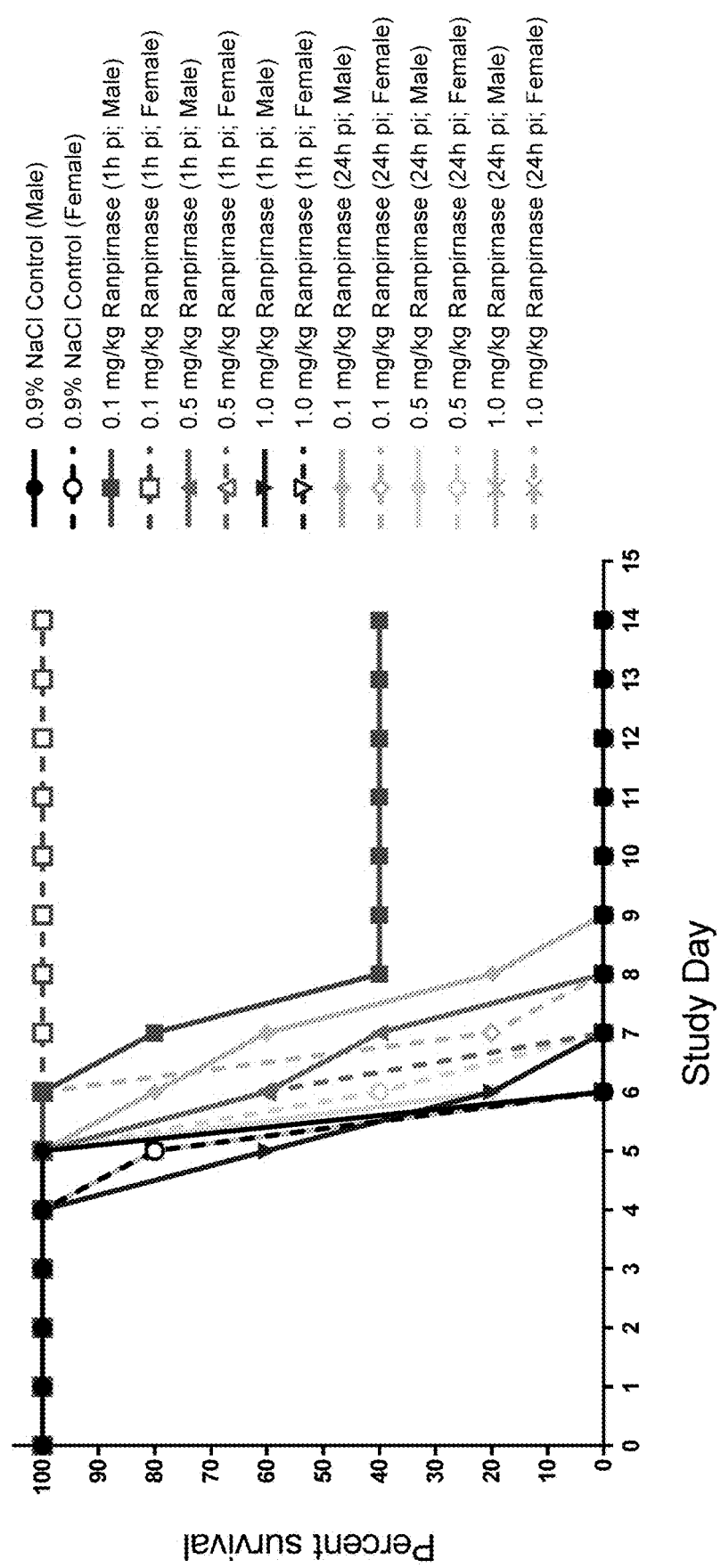
FIG. 31 is a graph showing that survival of Ebola-infected BALB/c mice in the tested groups occurs in ranpirnase-treated mice of both sexes.
Figure 32:
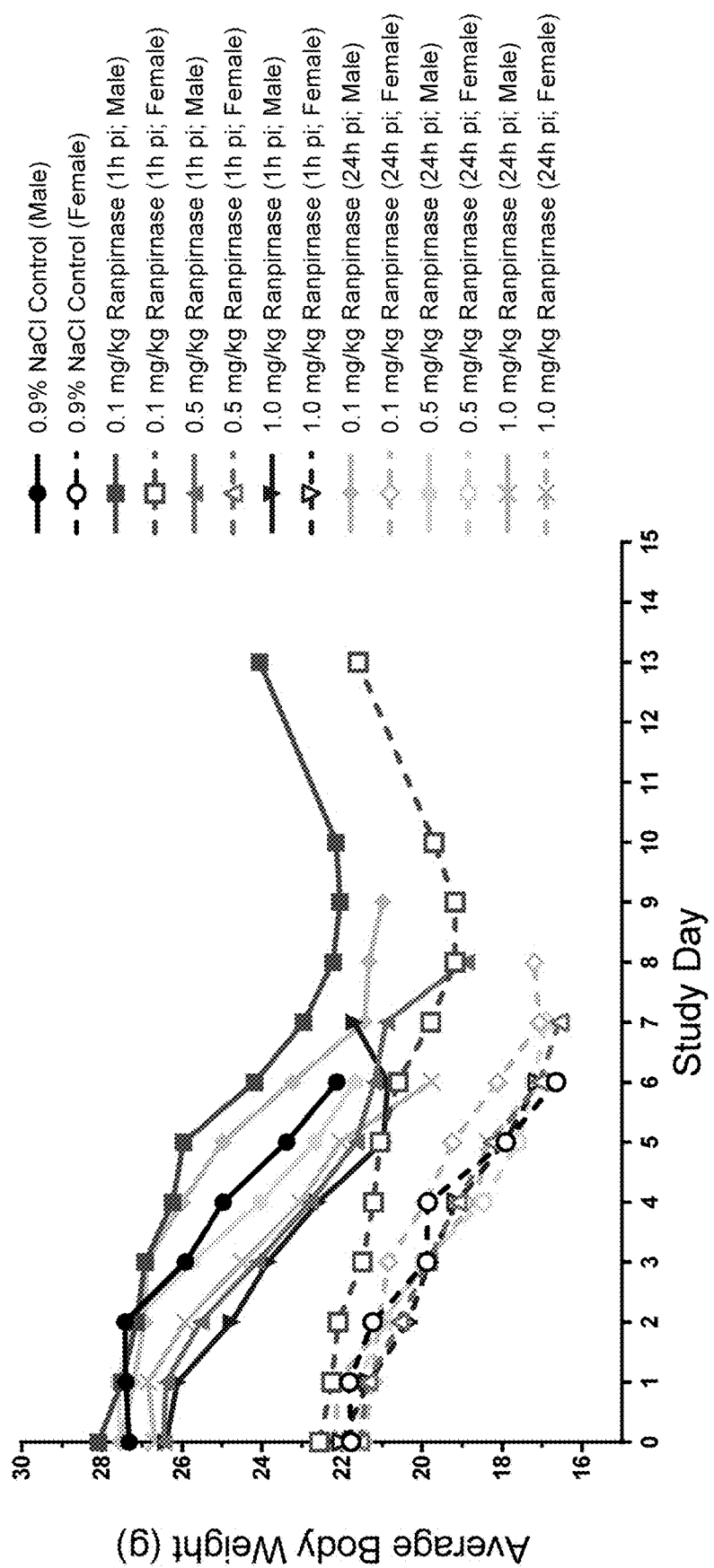
FIG. 32 is a graph showing variation in body weight of Ebola-infected BALB/c mice in the tested groups during the experiment.

As can be seen in FIGS. 30, 31, and 32, relative to saline-treated animals, treatment with 0.1 mg/kg ranpirnase gave longer survival times with fewer deaths and longer survival to euthanasia, with slower body weight loss and fewer clinical signs of decreased activity and poor appearance. This effect was observed when treatment began at both 1 hour and 24 hours post infection although the effect was less for the 24 hour group. 0.5 mg/kg ranpirnase treatment gave less effect than 0.1 mg/kg, and the 1 mg/kg group was less effective than the 0.5 mg/kg group. Females seemed to be slightly better at responding to ranpirnase treatment at each dose level.

Surprisingly, it appeared that lower doses of ranpirnase were more effective than higher doses. The reason for this is not known. It may be due to the study design, which required that animals be euthanized when they lost more than 20% of their body weight. Had the animals been given supportive therapy and allowed to remain on study (Ebola patients are given supportive therapy regardless of their weight loss) they may have regained weight and been restored to health.

Figure 33:
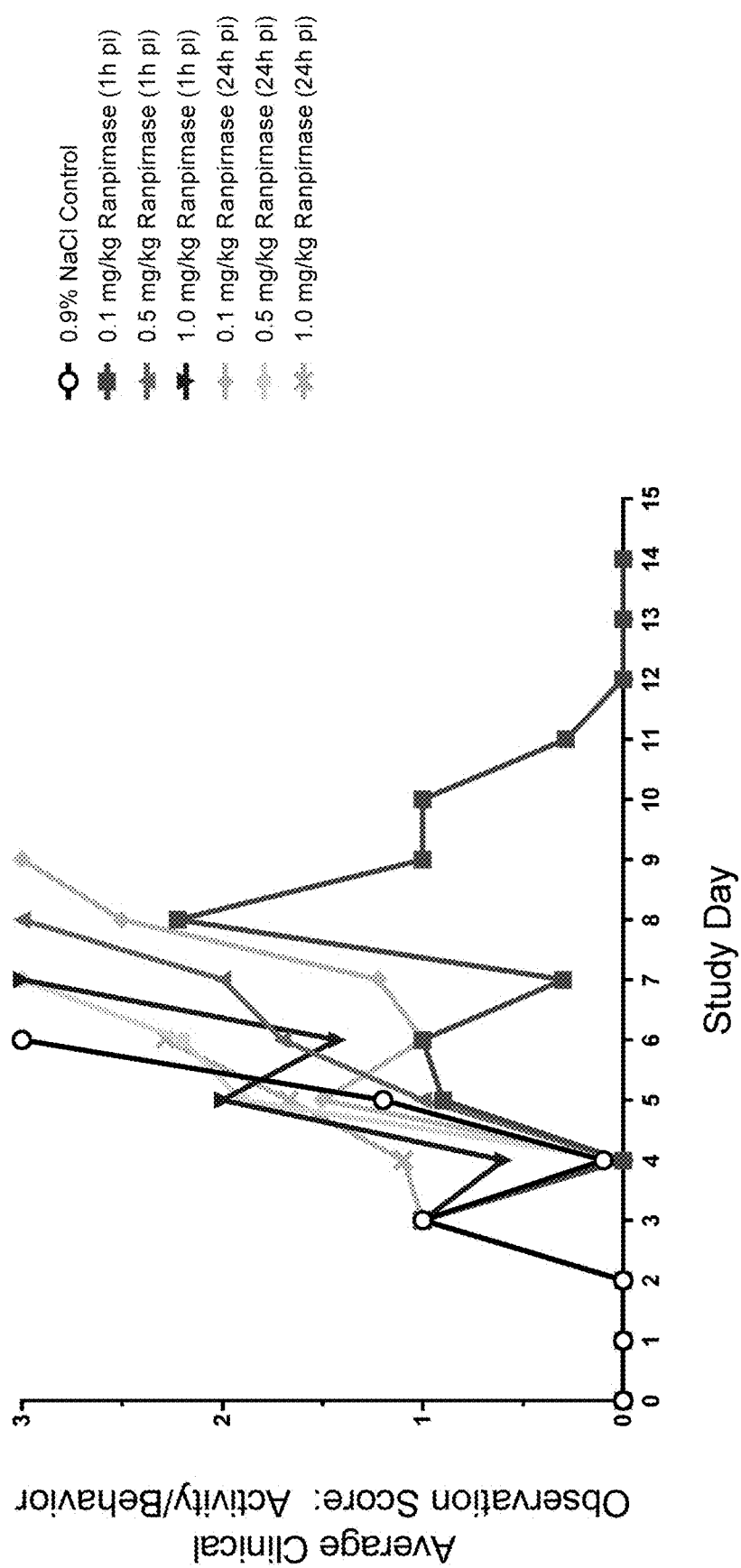
FIG. 33 is a graph showing variation in the activity/behavior of Ebola-infected BALB/c mice in the tested groups during the experiment.

Such a possible result (increased weight and improved health) is suggested by the experimental results illustrated in FIGS. 33 and 34. During this experiment, the activity/behavior and the appearance of the animals was monitored. In FIG. 33:

an activity/behavior score of 0 corresponds to normal behavior/response to external stimuli;

an activity/behavior score of 1 corresponds to minor changes in behavior or exaggerated responses to external stimuli;

an activity/behavior score of 2 corresponds to less mobile, less alert, inactive when activity expected, moderate abnormal response to external stimuli; and an activity/behavior score of 3 corresponds to moribund: minimal to no activity, mobility consistent with inability to reach food or water.

In FIG. 34:

an appearance score of 0 corresponds to normal;

an appearance score of 1 corresponds to lack of grooming;

an appearance score of 2 corresponds to coat rough, possible nasal and/or ocular discharge, ataxia, labored/irregular breathing, slightly hunched posture, partial paralysis; and an appearance score of 3 corresponds to coat very rough, abnormal/hunched posture, paralysis, seizures, weight loss exceeding 20% of body weight.

As can be seen in FIGS. 33 and 34, some of the animals showed only mild abnormalities in activity/behavior and in appearance at the time they were euthanized. It will be understood that when living animals are used in medical research, an institutional animal care and use committee ("IACUC") establishes standards that define the boundaries of humane treatment of the experimental subjects. In this study, the IACUC determined that it would be inhumane to allow mice to continue to live once they had lost more than 20% of their body weight. Hence, their apparent activity and health notwithstanding, mice were euthanized once this degree of weight loss occurred.

This experiment demonstrated that therapeutic administration of ranpirnase effectively promotes survival of mice that are infected with the Ebola virus at the time the ranpirnase is administered. This is true even when the Ebola virus has remained untreated for as long as 24 hours. Animal testing showing such extended survival shows that ranpirnase treatment is reasonably correlated with usefulness in therapeutically treating patients that are infected with the Ebola virus at the time the treatment is administered. This still further evidences the likelihood that systemically administered ranpirnase will be useful in therapeutically treating a mammalian subject infected with a virus, and particularly a mammalian subject infected with Ebola virus.

In summary: there is now a body of confirmatory in vitro and in vivo data demonstrating that administration of ranpirnase is active against EBOV. This is true whether the ranpirnase is administered prophylactically or therapeutically. A person of ordinary skill in this art would regard such confirmatory in vitro and in vivo data as powerful evidence of usefulness of ranpirnase in treating EBOV in a mammalian subject.

Example 6: AV in NHBE Cells

A study was conducted to evaluate the anti-adenoviral activity of ranpirnase in NHBE cells.

Ranpirnase stock solution was prepared at 200 µM and stored in aliquots at −80° C. On the first day of the experiment, one aliquot was thawed and working solutions were prepared by appropriately diluting the stock concentration in cell culture medium. Working solutions were pre-warmed in a water bath set to 37° C. for 15-30 minutes prior to use.

Differentiated NHBE cells (MatTek Corporation, Ashland, Mass.) were used in the study. Cells were provided in kits with 12 or 24 tissue inserts each. The kits used in the study (EpiAirway™, AIR-110, and AIR-100, respectively) originated from a single human donor, #9831, a 23-year old, healthy, non-smoking, Caucasian male. Upon arrival, tissue inserts were immediately transferred to individual wells of a 6-well plate according to manufacturer's instructions. Tissues were supplied with 1 ml of MatTek's culture medium (AIR-100-MM/Maintenance Medium) to the basolateral side, whereas the apical side was exposed to a humidified 95% air/5% $CO_2$ environment. Cells were equilibrated at 37° C. for at least 16 hours before the start of the experiment. After the equilibration period, the mucin layer, secreted from the apical side of the cells, was removed by repeated (3×) careful washing with 500 µl pre-warmed 30 mM HEPES Buffered Saline Solution (Lonza, CC-5024/Lot 0000354165) and the culture medium was replenished.

The virus (adenovirus 2, strain Miller from ATCC; titer 6.7 log 10 $CCID_{50}$/0.1 ml) was stored at −80° C. prior to use. The dose level of adenovirus corresponded to an MOI of 0.1.

Differentiated NHBE cells were experimentally infected with the virus. After an adsorption period of 1 hour, the viral inoculum was removed and treatments were applied as shown in FIG. 21. Twenty-four hours post infection, treatments were replenished in the basal compartment of the tissue inserts. Five days post infection, supernatants were harvested and stored at −80° C. until determination of virus titers in A-549 cells (human lung carcinoma cells from ATCC). Controls included four groups:

Group 1—infected and placebo-treated cells (virus control);

Group 2—sham-infected and treated cells (toxicity controls);

Group 3—sham-infected and placebo-treated cells (cell control); and

Group 4—2',3'-dideoxycytidine as a positive control drug. Toxicity controls were microscopically examined for possible changes in tissue and/or cell morphology at the end of the experiment.

NHBE cells were inoculated by exposure of the apical side to AV or cell culture medium (sham) as shown in FIG. 21. After 1 hour±10 min of incubation at 37° C. and 5% $CO_2$, the viral inoculum or cell culture medium was removed from the cells. The apical side of the cells was washed once with 500 µl pre-warmed HEPES Buffered Saline Solution.

After inoculation, ranpirnase, 2',3'-dideoxycytidine, or cell culture medium (placebo/cell control) was added to the apical side of the cells and in the basal medium compartment, and incubated with the cells for 1 hour. After 1-hour incubation, the drug-containing medium was removed from the apical and basal chambers. Culture medium alone (placebo/cell control) or with drug (test condition) was added to the bottom chamber, and cells were incubated for 4 days. Twenty-four hours post infection, cell culture medium with and without drug was replenished to the basal compartment.

Following infection and treatment, cells were maintained at the air-liquid interface, and cell culture supernatant was harvested 48 hours post infection. Virus released into the apical compartment of the NHBE cells was harvested by the addition and collection of 500 µl culture medium allowed to equilibrate for 30 min at 37° C. and 5% $CO_2$. The medium from the apical compartment was divided into 2 aliquots, which were stored at −80° C. for future analysis of viral titers.

To assess the virus dose that was able to infect 50% of the cell cultures ($CCID_{50}$), A-549 cells were seeded in 96-well plates and grown overnight to achieve confluence, then washed twice with 100 µl infection medium (DMEM/EBSS supplemented with 50 µl/ml gentamycin). Wells were filled with 100 µl infection medium. Apical washes from the NHBE cell cultures were diluted 10-fold in infection medium and 100 µl were transferred into respective wells of a 96-well microtiter plate. Each concentration of ranpirnase from the NHBE cells (6 NHBE cell wells/dose) was titered leading to six titers per concentration (each NHBE well treated as a replicate) to evaluate the virus yields from infected and infected, treated cells. Thus, each concentration of ranpirnase was titered a total of six times. For the positive control, 2'3'-dideoxycytidine, one well of NHBE cells only was assigned to each concentration. Thus, each concentration was titered only once. Three wells were assigned as untreated, infected controls. They were titered once, resulting in three replicate untreated, infected control titers. After 6 days of incubation at 37° C. and 5% $CO_2$, cells were microscopically examined and scored for virus-induced cytopathic effect ("CPE"). A well was scored positive if any trace of CPE (usually cell rounding or lysis) was observed as compared with the uninfected control. $CCID_{50}$ was calculated by the Reed-Muench method.

Figure 22:
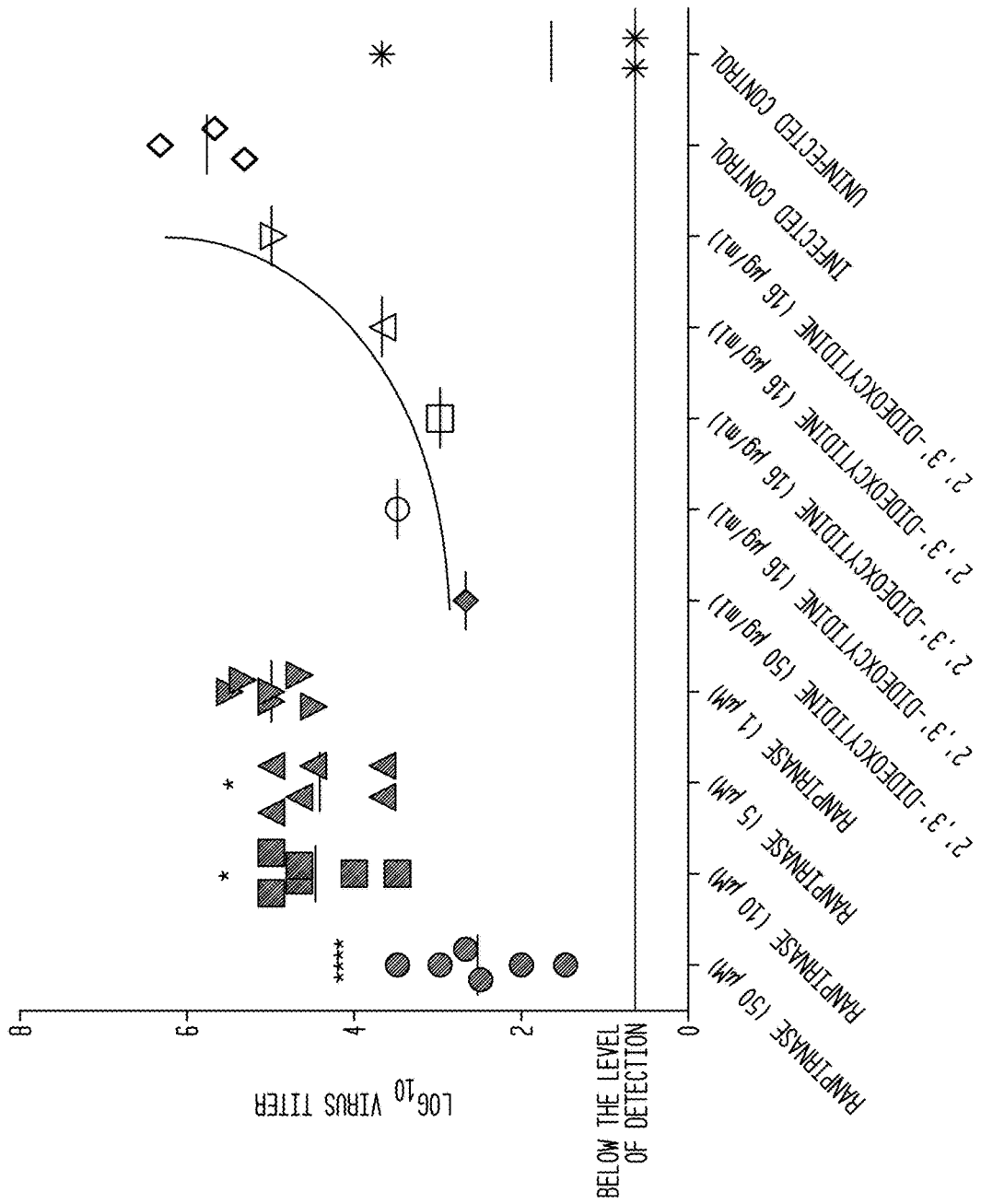
FIG. 22 shows the results of the study of FIG. 21.

The results of the study are provided in FIG. 22. All treatments with ranpirnase decreased virus titers to undetectable levels, except for the lowest dose. This reduction represented an approximately three log drop in virus titer for the 50 μM ranpirnase treatment (four asterisks indicates that $p<0.0001$ as compared to placebo). For the 5 and 10 μM ranpirnase treatments, a ~1 log reduction in virus titers was detected when compared to the virus titers detected from the untreated, infected controls wells (a single asterisk indicates that $p<0.05$ as compared to placebo). 2'3'-dideoxycytidine inhibited virus replication as expected.

No virus cytopathic effects were detected in uninfected, ranpirnase-treated or 2'3'-dideoxycytidine-treated cells. Microscopy evaluations of ranpirnase-treated or 2'3'-dideoxycytidine-treated NHBE cells revealed no toxicological phenomena.

Therefore, the results of the study showed that all higher doses of ranpirnase treatment reduced AV titers in a statistically significant manner. Such reduction of viral titers of AV virus without cytopathic effects on the host cells is reasonably correlated with usefulness of ranpirnase in treating AV. Because ranpirnase was effective at inhibiting replication of AV in NHBE cells while not killing the host cells, this experiment further evidences the likelihood that systemically administered ranpirnase will be useful in treating a mammalian subject infected with a virus, and particularly a mammalian subject infected with AV. Furthermore, the above-disclosed experimental results in VEEV, CHIV, and EBOV indicate that it should be possible to use ranpirnase as a prophylactic to prevent AV infection.

Example 7: Canine Parvovirus in A-72 Cells

Canine parvovirus type 2c was grown in A-72 cell cultures and virus contained in cell culture medium (Dulbecco's minimum essential medium; "DMEM") was stored frozen at −80° C. until used. The titer of the virus stock was about 105 cell culture infectious dose units/ml, with a hemagglutination (HA) titer of 1,024 to 2,048.

The A-72 continuous cell line, a fibroblastic line derived from a canine tumor, was grown in DMEM in 96-well plates, allowing for various conditions to be tested.

To assess the cytotoxicity of ranpirnase in A-72 cells, A-72 cells were seeded into a 24-well plate at a concentration of 125,000 cells/well in a volume of 1 ml of DMEM. The medium in each well was supplemented with 25 μl of ranpirnase to concentration of 5 μg/ml, 1 μg/ml, 0.5 μg/ml and 0.1 μg/ml. Each concentration was tested in 4 replicates. After incubating at 35.5° C. for 4 days, the cells were examined under an inverted microscope for any visual morphologic changes.

Next, the efficacy of ranpirnase was assessed. Ranpirnase was tested at various concentrations ranging from 10 μg/ml down to 0.15625 μg/ml in 2-fold dilutions. Stock virus was tested from undiluted through a dilution of 1/10,000. A-72 cells were trypsinized following standard procedures and seeded into 96-well cell culture plates at a concentration of 18,750 cells/well in a volume of 150 μl. Ranpirnase was then added to each well to attain a final pre-determined concentration. After incubating for 2 hours at 35.5° C., 25 μl of virus at various dilutions was added. Controls included ranpirnase-treated/uninfected cells and ranpirnase inhibition of canine parvovirus replication in cell cultures of untreated/uninfected cells. All variables were tested in duplicate. At the end of 4 days of incubation at 35.5° C., the supernatant fluid was harvested and tested for evidence of virus replication using the HA test (which tests the ability of the virus to agglutinate a 0.5% suspension of swine red blood cells). HA titers were expressed as the reciprocal of the highest dilution of supernatant fluid that induced visual agglutination of the red blood cells in a 96-well plate.

When ranpirnase-treated (various concentrations) and untreated cells were microscopically examined, there was no visual difference in morphology between the two groups, regardless of ranpirnase concentration. Thus, there was no apparent cytotoxic effect of ranpirnase at any of the concentrations tested.

The results of the study are provided in FIG. 23. Virus growth was detected in untreated cell cultures up to a virus dilution of 1/100. Virus growth was also detected when the undiluted virus stock was used to infect cell cultures treated with 0.15625 μg/ml. There was no virus growth in cultures treated with a ranpirnase concentration of 0.3125 μg/ml or higher. Inhibition of viral growth of canine parvovirus without cytotoxic effects on the host cells is reasonably correlated with usefulness of ranpirnase in treating canine parvovirus. Because ranpirnase was so effective at inhibiting viral growth of canine parvovirus while not killing the host cells, this experiment further evidences the likelihood that systemically administered ranpirnase will be useful in treating a mammalian subject infected with a virus, and particularly a mammalian subject infected with canine parvovirus. Furthermore, the above-disclosed experimental results in VEEV, CHIV, and EBOV indicate that it should be possible to use ranpirnase as a prophylactic to prevent canine parvovirus infection.

Example 8: RSV in NHBE Cells

Ranpirnase stock solution was prepared, stored, thawed, and used to prepare working solutions as described in the AV experiment disclosed above.

NHBE cells from MatTek Corporation were used in the study. They were the same cell line as was used in the AV experiment discussed above and were provided in the same kits. As in the AV experiment, tissue inserts were immediately transferred to individual wells of a 6-well plate according to manufacturer's instructions. Tissues were supplied with 1 ml of the same culture medium used in the AV experiment to the basolateral side, and the apical side was exposed to a humidified 95% air/5% $CO_2$ environment. Cells were equilibrated as in the AV experiment, and after this equilibration period, the mucin layer was removed as in the AV experiment and the culture medium was replenished.

The virus (RSV A2 from ATCC; titer 4.7 log 10 $CCID_{50}$/ 0.1 ml) was stored at −80° C. prior to use. The dose level of challenge virus corresponds to an MOI of 0.1.

Differentiated NHBE cells were experimentally infected with the RSV virus. After an adsorption period of 1 hour, the viral inoculum was removed and treatments were applied as shown in FIG. 24. Twenty-four hours post infection, treatments were replenished in the basal compartment of the tissue inserts. Forty-eight hours post infection, supernatants were harvested and stored at −80° C. until determination of virus titers in MA-104 cells (embryonic African green monkey kidney cells from ATCC). Controls consisted of three of the four groups used in the AV experiment:
Group 1—infected and placebo-treated cells (virus control);
Group 2—sham-infected and treated cells (toxicity controls); and
Group 3—sham-infected and placebo-treated cells (cell control). Toxicity controls were microscopically examined for possible changes in tissue and/or cell morphology at the end of the experiment.

NHBE cells were inoculated by exposure of the apical side to RSV or cell culture medium (sham) as shown in FIG. 24. After 1 hour±10 min of incubation at 37° C. and 5% $CO_2$, the viral inoculum or cell culture medium was removed from the cells. The apical side of the cells was washed once with 500 µl pre-warmed HEPES Buffered Saline Solution.

After inoculation, ranpirnase, or cell culture medium (placebo/cell control) was added to the apical side of the cells and in the basal medium compartment, and incubated with the cells for 1 hour. After 1-hour incubation, the drug-containing medium was removed from the apical and basal chambers. Culture medium alone (placebo/cell control) or with drug (test condition) was added to the bottom chamber, and cells were incubated for an additional 23 hours (24 hour total post-infection incubation). Twenty-four hours post infection, cell culture medium with and without drug was replenished to the basal compartment.

Following infection and treatment, cells were maintained at the air-liquid interface, and cell culture supernatant was harvested 48 hours±30 min post infection. Virus released into the apical compartment of the NHBE cells was harvested by the addition and collection of 500 µl culture medium allowed to equilibrate for 30 min at 37° C. and 5% $CO_2$. The medium from the apical compartment was divided into 2 aliquots, which were stored at −80° C. for future analysis of viral titers. Images of one replicate tissue insert per treatment were taken with an inverted microscope at 40 and 100×, respectively, prior to harvest.

To assess the $CCID_{50}$, MA-104 cells were seeded in 96-well plates and grown overnight to achieve confluence, then washed twice with 100 µl infection medium (MEM/EBSS supplemented with 50 µl/ml gentamycin). Wells were filled with 100 µl infection medium. Apical washes were diluted 10-fold in infection medium and 100 µl were transferred into respective wells of a 96-well microtiter plate. Each sample was titered in triplicate (Passage 1) to evaluate the virus yields from infected and infected, treated cells. After 6 days of incubation at 37° C. and 5% CO2, cells were microscopically examined and scored for virus-induced cytopathic effect (CPE). A well was scored positive if any trace of cytopathic effect (usually cell rounding or syncytium) was observed as compared with the uninfected control. CCID50 was calculated by the Reed-Muench method.

Figure 25:
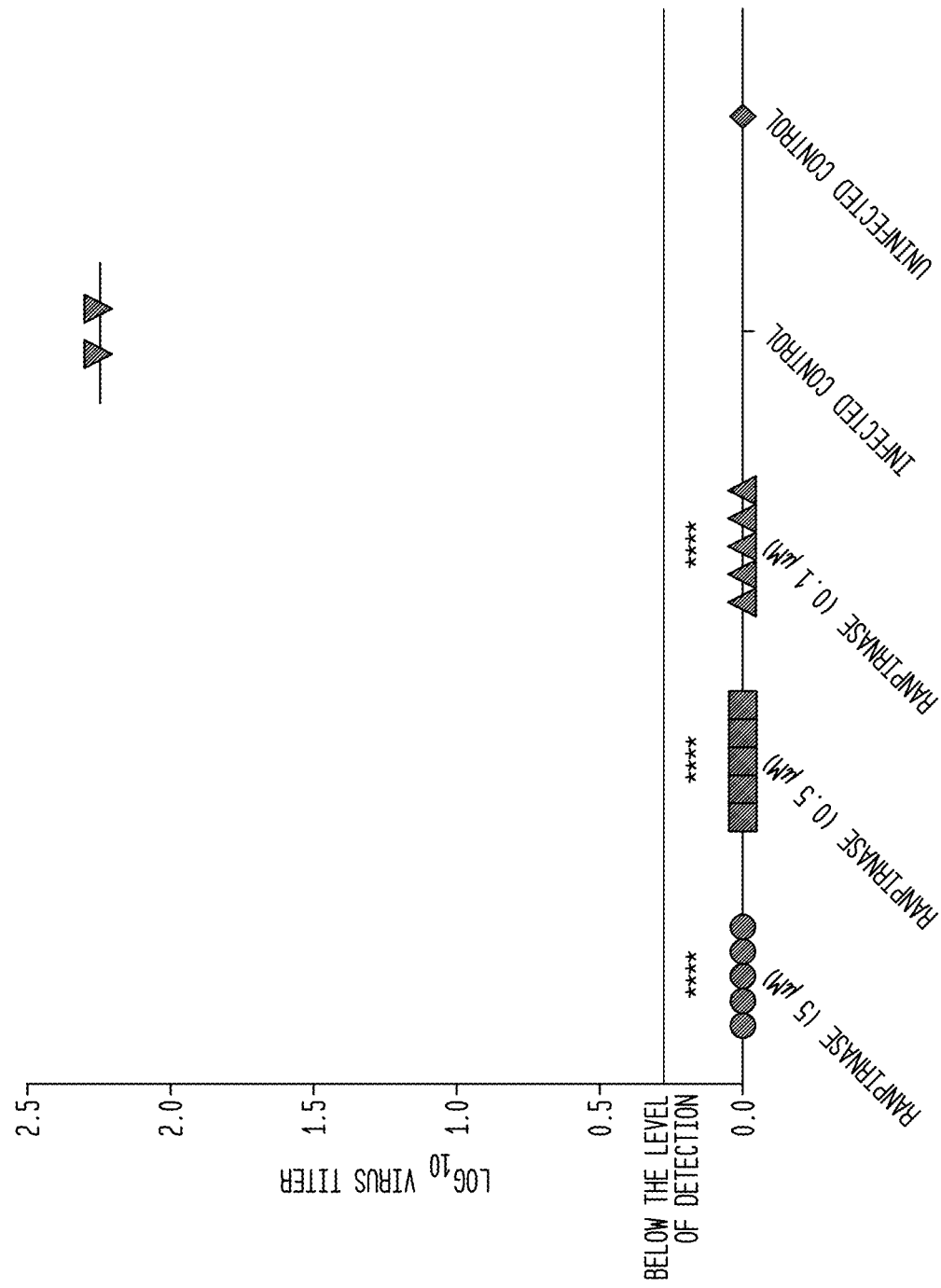
FIG. 25 shows the results of the study of FIG. 24.

The results of the study are provided in FIG. 25. Results were analyzed for statistical significance by one-way ANOVA (GraphPad Prism, version 6c). All treatments with Ranpirnase decreased virus titers to undetectable levels (FIG. 25). This reduction represented a 2.3 log reduction in virus titers compared to untreated, infected controls (the four asterisks shown in FIG. 25 indicate that p<0.0001).

No virus cytopathic effects were detected Ranpirnase-treated/sham infected cells or uninfected control cells. Microscopy evaluations of sham infected, Ranpirnase-treated or 2'3'-dideoxycytidine-treated NHBE cells revealed no toxicological phenomena.

Therefore, the results of the study showed that all doses of ranpirnase tested (5 µM, 0.5 µM, and 0.1 µM) reduced RSV titers in a statistically significant manner, and that ranpirnase alone did not elicit cytopathic effects in NHBE cells. Such reduction of viral titers without accompanying cytopathic effects on the host cells is reasonably correlated with usefulness of ranpirnase in treating RSV. Because ranpirnase was so effective at inhibiting RSV while not killing the host cells, this experiment further evidences the likelihood that systemically administered ranpirnase will be useful in treating a mammalian subject infected with a virus, and particularly a mammalian subject infected with RSV. Furthermore, the above-disclosed experimental results in VEEV, CHIV, and EBOV indicate that it should be possible to use ranpirnase as a prophylactic to prevent RSV infection.

Example 9: RV in NHBE Cells

Ranpirnase stock solution was prepared, stored, thawed, and used to prepare working solutions as described in the AV and RSV experiments disclosed above.

NHBE from MatTek Corporation were used in the study. They were the same cell line as were used in the AV and RSV experiments discussed above and were provided in the same kits. As in the AV and RSV experiments, tissue inserts were immediately transferred to individual wells of a 6-well plate according to manufacturer's instructions. Tissues were supplied with 1 ml of the same culture medium used in the AV and RSV experiments to the basolateral side, and the apical side was exposed to a humidified 95% air/5% $CO_2$ environment. Cells were equilibrated as in the AV experiment, and after this equilibration period, the mucin layer was removed as in the AV and RSV experiments and the culture medium was replenished.

RV-14 (strain 1059 from ATCC) was stored at −80° C. prior to use. The titer of the stock virus was equal to titer 3.6 log 10 CCID50/0.1 ml. The dose level of challenge virus was based on data from the previous experiments, and corresponded to a multiplicity of infection (MOI) of 0.0041.

Differentiated NHBE cells were experimentally infected with RV-14 virus. After an adsorption period of 1 hour, the viral inoculum was removed and treatments applied (FIG. 26). Twenty-four hours post infection, treatments were replenished in the basal compartment of the tissue inserts. Four days post infection, supernatants were harvested and stored at −80° C. until determination of virus titers in HeLa-Ohio-1 cells (human cervical carcinoma cells from ATCC). Controls consisted of four groups:

Group 1—infected and placebo-treated cells (virus control);

Group 2—sham-infected and treated cells (toxicity controls);

Group 3—sham-infected and placebo-treated cells (cell control); and

Group 4—pirodavir as a positive control drug.

Toxicity controls were microscopically examined for possible changes in tissue and/or cell morphology at the end of the experiment.

NHBE cells were inoculated by exposure of the apical side to RV-14 or cell culture medium (sham infection) as seen in FIG. 27. After 1 hour±10 min of incubation at 37° C. and 5% $CO_2$, the viral inoculum or cell culture medium was removed from the cells. The apical side of the cells was washed once with 500 μl pre-warmed HEPES Buffered Saline Solution.

After inoculation, ranpirnase, pirodavir, or cell culture medium (placebo/cell control) was added to the apical side of the cells and in the basal medium compartment, and incubated with the cells for 1 hour. After 1-hour incubation, the drug-containing medium was removed from the apical and basal chambers. Culture medium alone (Placebo/Cell control) or with drug (test condition) was added to the bottom chamber, and cells were incubated for 4 days. Twenty-four hours post infection, cell culture medium with and without drug was replenished to the basal compartment.

Following infection and treatment, cells were maintained at the air-liquid interface, and cell culture supernatant was harvested 4 days post virus exposure. Virus released into the apical compartment of the NHBE cells was harvested by the addition and collection of 500 µl culture medium allowed to equilibrate for 30 min at 37° C. and 5% $CO_2$. The medium from the apical compartment divided into 2 aliquots, which were stored at −80° C. for future analysis of viral titers.

HeLa Ohio-1 cells were seeded in 96-well plates and grown overnight to achieve confluence, then washed twice with 100 µl infection medium (MEM/EBSS supplemented with 50 µl/ml gentamycin). Wells were filled with 100 µl infection medium. Apical washes from the NHBE cell cultures were diluted 10-fold in infection medium and 100 µl were transferred into respective wells of a 96-well microtiter plate. Each concentration of ranpirnase from the NHBE cells (6 NHBE cell wells/dose) was titered leading to six titers per concentration (each NHBE well treated as a replicate) to evaluate the virus yields from infected and infected, treated cells. Thus, each concentration of Ranpirnase was titered a total of six times. For the positive control, pirodavir, one well of NHBE cells only was assigned to each concentration. Thus, each concentration was titered only once. Three wells were assigned as untreated, infected controls. They were titered once, resulting in three replicate untreated, infected control titers. After 7 days of incubation at 37° C. and 5% $CO_2$, cells were microscopically examined and scored for virus-induced CPE. A well was scored positive if any trace of CPE (cell lysis) was observed as compared with the uninfected control. CCID50 was calculated by the Reed-Muench method and the inverse of that dilution represented the virus titer.

Figure 27:
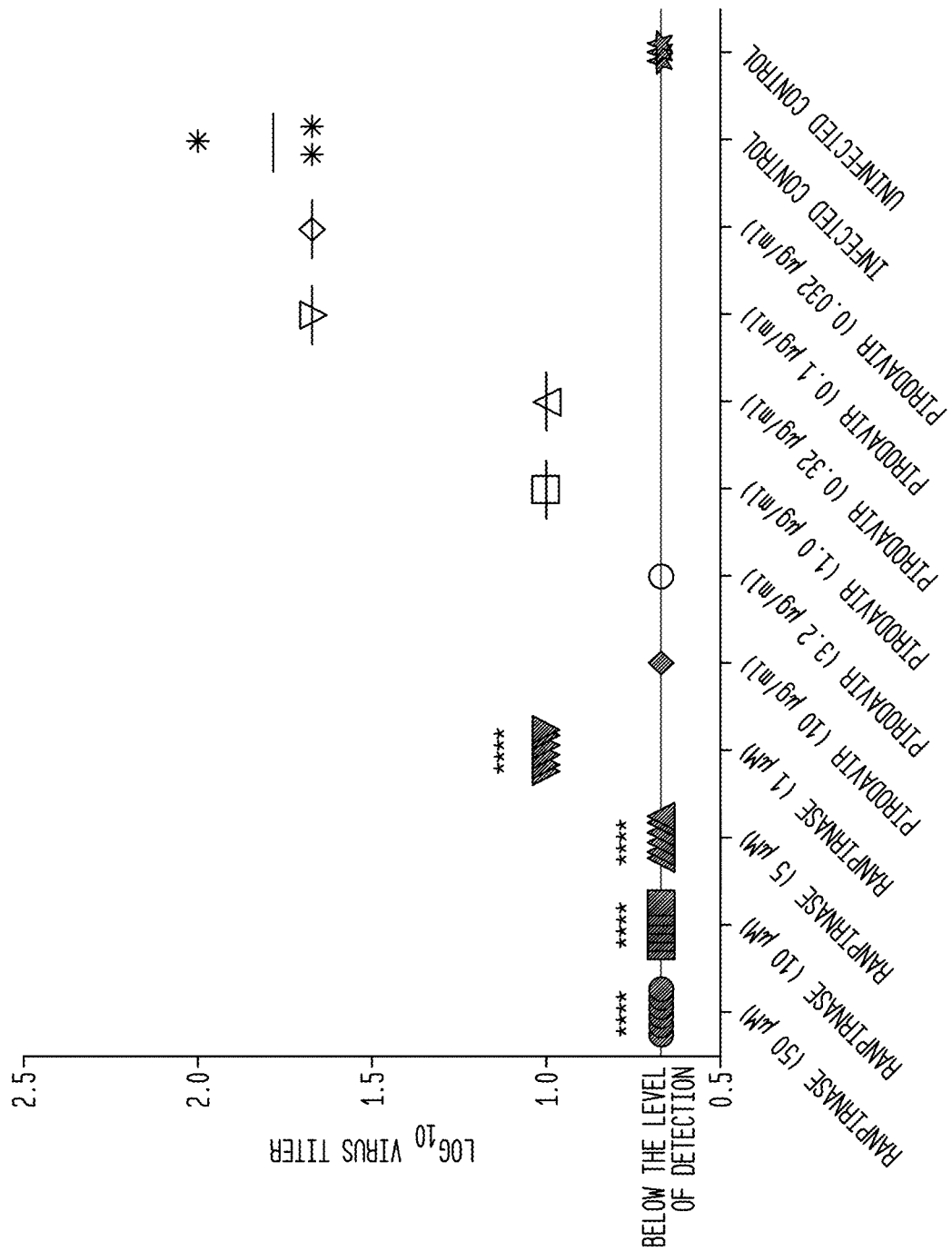
FIG. 27 shows the results of the study of FIG. 26.

All ranpirnase treatments decreased virus titers relative to the titers of untreated infected controls except for the lowest dose (FIG. 27). The reduction in virus titer with 50, 10, 5 µM ranpirnase treatment represented an approximate 1.67 log 10 drop in virus titer for the (P<0.0001). For the 1 µM ranpirnase treatment, an ~1 log reduction in virus titers was detected when compared to the virus titers detected from the untreated, infected controls wells (P<0.0001). Pirodavir inhibited virus replication as expected at 10 and 3.2 µg/ml with a somewhat dose responsive decrease in virus yields at subsequent lower dilutions of drug. Typically at 0.0032 µg/ml, pirodavir is also inactive against RV-14 in a HeLa Ohio-1 cell culture antiviral system as was seen in NHBE cells in this experiment.

No virus cytopathic effects were detected in uninfected, ranpirnase-treated or pirodavir-treated cells. Microscopy evaluations of ranpirnase-treated or pirodavir-treated NHBE cells revealed no toxicological phenomena.

Therefore, the results of the study showed that all doses of ranpirnase tested (50 µM, 1.0 µM, 5 µM and 1 µM) reduced RV-14 titers in a statistically significant manner, and that ranpirnase alone did not elicit cytopathic effects in NHBE cells. Such titer reduction, accompanied by absence of cytopathic effects on the host cells, is reasonably correlated with usefulness of ranpirnase in treating RV-14. Because ranpirnase was so effective at inhibiting RV-14 while not killing the host cells, this experiment further evidences the likelihood that systemically administered ranpirnase will be useful in treating a mammalian subject infected with a virus, and particularly a mammalian subject infected with RV-14. Furthermore, the above-disclosed experimental results in VEEV, CHIV, and EBOV indicate that it should be possible to use ranpirnase as a prophylactic to prevent RV-14 infection.

Example 10: Vaccinia in Vero 76 Cells

Ranpirnase stock solution was prepared, stored, thawed, and used to prepare working solutions as described in the AV, RSV, and RV-14 experiments disclosed above.

The virus (vaccinia, strain WR from ATCC) was stored at −80° C. prior to use. The titer of the stock virus was equal to titer 7.7 log 10 CCID50/0.1 ml. The dose level of challenge virus was based on data from other experiments, and corresponded to 50-100 viral plaques/well.

To determine the antiviral effect of ranpirnase against vaccinia, Vero 76 cells in 24 well plates were experimentally infected with virus in the format shown in FIG. 28. Controls consisted of four groups:

Group 1—infected and placebo-treated cells (virus control);
Group 2—sham-infected and treated cells (toxicity controls);
Group 3—sham-infected and placebo-treated cells (cell control); and
Group 4—cidofovir as a positive control drug.

Toxicity controls were microscopically examined for possible changes in tissue and/or cell morphology at the end of the experiment and for staining intensity by crystal violet.

The assay was done in Vero 76 cells in 24-well plates as described above in FIG. 28. The virus was pre-titrated to produce 50-100 viral plaques in 48 hours and absorbed to the cells for 1 hour at 37° C. The virus inoculum was then removed and test compounds in agarose (described below) were added to the wells where appropriate.

Dilutions of Ranpirnase and cidofovir (the positive control) were made using a half-log 10 dilution series (FIG. 28). Two microwells were used per dilution. The medium for these assays contained 1% final concentration of agarose (Sea Plaque agarose from FMC Corp.) in 2% FBS in MEM. The agar overlay containing test compound, positive control compound, or no compound (virus control) was hardened in the refrigerator for 5-10 minutes prior to incubation at 37° C. At 2 days post virus exposure, the wells of each plate were overlaid with 1 ml of 10% buffered formalin to fix the cells to the wells. Then the agar overlays were removed. The wells were stained with 0.1% crystal violet and the plaques were counted with the aid of a plaque viewer at either 13× magnification. The concentration of inhibitor reducing plaque numbers by 50% (EC50 value) was determined by plotting inhibitor concentration versus percentage of plaques. The determination of toxicity was done by examining the density of staining of the monolayers designated for toxicity evaluation. The less intense the staining compared to sham, untreated cells, the greater the toxicity. There was no toxicity detected by this procedure and thus it was unnecessary to calculate a CC50 value.

The antiviral effect of ranpirnase against vaccinia infection in Vero 76 cells was evaluated. Neither ranpirnase nor cidofovir was toxic at the dilutions used in the assay (FIG. 29), which was in harmony with other previous studies in which toxicity for both drugs was quantified by neutral red uptake assay.

Ranpirnase strongly inhibited vaccinia replication at a good potent dose of 3.8 μM, which compared favorably with cidofovir (EC50=10 μM), the drug that is stockpiled by the Defense Department for use in case of a smallpox outbreak. Since ranpirnase was not toxic at 100 μM, it was highly selective in its inhibition of virus (SI>26).

Because SI measures the ability of a substance under test to inhibit replication of a particular virus without killing the infected cells themselves, it is reasonably correlated with usefulness of the substance in treating a mammalian subject that is infected with the virus. Accordingly, test results in which SI>1 indicate that mammalian subjects infected with vaccinia can be treated by systemic administration of an appropriate dose of ranpirnase. Furthermore, other above-disclosed experimental results in VEEV, CHIV, and EBOV indicate that it should be possible to use ranpirnase as a prophylactic to prevent vaccinia infection.

All the above data except those relating to VEEV and canine parvovirus are reasonably correlated with activity against viral infections in humans. These data constitute strong evidence that ranpirnase will be active against viruses in humans. The data relating to VEEV are reasonably correlated with activity against a VEEV infection in an equine species, and the data relating to canine parvovirus are reasonably correlated with activity against a canine parvovirus infection in dogs and other mammals.

The above-disclosed AV data were acquired using adenovirus-2, which is a member of the adenoviridae family of viruses. The viruses in this family are very closely related and the demonstrated antiviral activity of ranpirnase against any one virus within the adenoviridae family is strong evidence that ranpirnase will have the same anti-replication activity against all viruses within the adenoviridae family.

The above-disclosed RV data were acquired using rhinovirus-14, an important member of the rhinovirus family of viruses. The viruses in this family are very closely related and the demonstrated antiviral activity of ranpirnase against any one virus within the rhinovirus family is strong evidence that ranpirnase will have the same anti-replication activity against all viruses within the rhinovirus family.

Vaccinia is a member of the poxvirus family of viruses. The viruses in the poxvirus family are very closely related and the demonstrated antiviral activity of ranpirnase against any one virus within the poxvirus family is strong evidence that ranpirnase will have the same antiviral activity against all viruses classified within the poxvirus family (specifically including smallpox, which is such a serious biohazard that it cannot prudently be tested in the laboratory).

Generally, in view of the different viruses that respond to treatment using ranpirnase, a person of ordinary skill in this art would conclude that any route by which ranpirnase is systemically administered will be adequate to treat any particular virus (although one route may be more effective than another in any particular instance). Thus, enteral administration (including without limitation oral administration and rectal administration) and parenteral administration (including without limitation intravenous administration, intramuscular administration, and aerosol delivery) are appropriate methods for administration of ranpirnase.

A therapeutically effective dose of ranpirnase can be determined by the skilled person as a matter of routine experimentation. The therapeutically effective dosage of a pharmaceutical composition can be determined readily by the skilled artisan, for example, from animal studies. Also, human clinical studies can be performed to determine the preferred effective dose for humans by a skilled artisan. Such clinical studies are routine and well known in the art. The precise dose to be employed will also depend on the route of administration. Effective doses may be extrapolated from dose-response curves derived from in vitro or animal test systems.

The above-recited experimental results were carried out using ranpirnase. However, other ribonucleases that are highly homologous to ranpirnase have exhibited highly similar activities against other viruses. These other ribonucleases are identified in U.S. Pat. Nos. 5,728,805, 6,239,257, and U.S. Pat. No. 7,229,824. The RNase of SEQ ID NO:2 in U.S. Pat. No. 5,728,805 is herein referred to as the "'805 variant", the RNase of SEQ ID NO:1 in U.S. Pat. No. 6,239,257 is herein referred to as "Amphinase 2", and the RNase of SEQ ID NO:59 of U.S. Pat. No. 7,229,824 is herein referred to as "rAmphinase 2". To a person of ordinary skill in this art, the similarities of homology and activity of these three other ribonucleases is strong evidence that these three other ribonucleases will have the same activity as ranpirnase has. Hence, although the above-disclosed experiments have not yet been repeated using the '805 variant, Amphinase 2, or rAmphinase 2, it is believed that the above data are fully applicable to these three ribonucleases and that these three ribonucleases will be active against rabies, MERS-CoV, influenza, CHIV, EBOV, AV, RSV, RV, and poxvirus in humans, VEEV in equine species, and canine parvovirus in dogs and other mammals.

As demonstrated above, ranpirnase inhibits growth of MERS-CoV, VEEV, and CHIV, and RV-14 in various cell types. These four viruses are all categorized in Baltimore Classification Group IV. This activity, taken together with the above-disclosed activity that ranpirnase has demonstrated against a broad spectrum of viruses, is substantial evidence justifying the conclusion that systemically administered ranpirnase will be effective against viruses categorized in Baltimore Classification Group IV. And, based upon the similarities of homology and activity of the '805 variant, Amphinase 2, and rAmphinase 2 to the homology and activity of ranpirnase, these three other ribonucleases would be expected to have the same activity as ranpirnase against viruses classified in Baltimore Classification Group IV.

As demonstrated above, ranpirnase inhibits growth of influenza, Ebola, measles, RSV, and rabies in various cell types. These five viruses are all categorized in Baltimore Classification Group V. This activity, taken together with the above-disclosed activity that ranpirnase has demonstrated against a broad spectrum of viruses, is substantial evidence justifying the conclusion that systemically administered ranpirnase will be effective against viruses categorized in Baltimore Classification Group V. And, based upon the similarities of homology and activity of the '805 variant, Amphinase 2, and rAmphinase 2 to the homology and activity of ranpirnase, these three other ribonucleases would be expected to have the same activity as ranpirnase against viruses classified in Baltimore Classification Group V.

Although at least one preferred embodiment of the invention has been described above, this description is not limiting and is only exemplary. The scope of the invention is defined only by the claims, which follow:

The invention claimed is:

1. A method of treating a viral infection in a mammalian patient, the viral infection being classified in Baltimore Classification Group V, comprising systemically administering a therapeutically effective dose of a therapeutic agent to the patient, wherein the therapeutic agent consists of ranpiranse.

2. A method of treating a rabies infection in a mammalian patient, comprising systemically administering a therapeutically effective dose of a therapeutic agent to the patient, wherein the therapeutic agent consists of ranpirnase.

3. The method of claim 1 or 2, wherein the patient is a human being.

4. A method of prophylactically protecting a patient from:
   a. rabies; or
   b. influenza; or
   c. respiratory syncytial virus; or,
   d. Ebola virus,
comprising the step of administering a therapeutically effective dose of ranpirnase to the patient.

5. A method of treating an Ebola infection in a mammalian patient, comprising systemically administering a therapeutically effective dose of ranpirnase to the patient.

6. A method of treating a respiratory syncytial infection in a mammalian patient, comprising systemically administering a therapeutically effective dose of a therapeutic agent to the patient, wherein the therapeutic agent consists of ranpirnase.

7. A method of prophylactically protecting a mammalian patient from a viral infection classified in Baltimore Classification Group V, comprising systemically administering a therapeutically effective dose of ranpirnase to the patient.

8. The method of claim 4, 5, 6, or 7, wherein the patient is a human being.

9. The method of claim 1, wherein the viral infection is an influenza infection.

10. The method of claim 1, wherein the viral infection is a measles infection.

\* \* \* \* \*